United States Patent
Braido et al.

(10) Patent No.: US 11,033,385 B2
(45) Date of Patent: Jun. 15, 2021

(54) STATIONARY INTRA-ANNULAR HALO DESIGNS FOR PARAVALVULAR LEAK (PVL) REDUCTION-PASSIVE CHANNEL FILLING CUFF DESIGNS

(71) Applicant: St. Jude Medical, Cardiology Division, Inc., St. Paul, MN (US)

(72) Inventors: Peter N. Braido, Wyoming, MN (US); Kent J. Smith, Shoreview, MN (US); Andrea L. McCarthy, Vadnais Heights, MN (US); Mina S. Fahim, Shoreview, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 110 days.

(21) Appl. No.: 16/246,714

(22) Filed: Jan. 14, 2019

(65) Prior Publication Data

US 2019/0142584 A1 May 16, 2019

Related U.S. Application Data

(63) Continuation of application No. 14/602,894, filed on Jan. 22, 2015, now abandoned.

(Continued)

(51) Int. Cl.
*A61F 2/24* (2006.01)

(52) U.S. Cl.
CPC .... *A61F 2/2418* (2013.01); *A61F 2210/0061* (2013.01); *A61F 2230/0095* (2013.01); *A61F 2250/001* (2013.01); *A61F 2250/0069* (2013.01)

(58) Field of Classification Search
CPC .. A61F 2/24; A61F 2/2418; A61F 2250/0069; A61F 2210/0061; A61F 2230/0095; A61F 2250/001
See application file for complete search history.

(56) References Cited

U.S. PATENT DOCUMENTS

| 3,657,744 A | 4/1972 | Ersek |
| 4,275,469 A | 6/1981 | Gabbay |

(Continued)

FOREIGN PATENT DOCUMENTS

| DE | 19857887 A1 | 7/2000 |
| DE | 10121210 B4 | 11/2005 |

(Continued)

OTHER PUBLICATIONS

International Search Report & Written Opinion for Application No. PCT/US2014/054485 dated Nov. 20, 2014.

(Continued)

*Primary Examiner* — Christopher D. Prone
(74) *Attorney, Agent, or Firm* — Lerner, David, Littenberg, Krumholz & Mentlik, LLP

(57) ABSTRACT

A prosthetic heart valve may include a collapsible and expandable stent extending in a flow direction between a proximal end and a distal end, a cuff attached to an annulus section of the stent, a plurality of prosthetic valve leaflets each having a belly attached to the cuff between a first location and a second location downstream of the first location in a flow direction, and a sealing structure attached to the annulus section of the stent. The annulus section of the stent may be adjacent the proximal end. The stent may include a plurality of struts shaped to form a plurality of cells connected to one another in a plurality of annular rows around the stent. The sealing structure may have a deployed condition with a diameter greater than a diameter of the proximal end of the stent when the stent is in an expanded use condition.

10 Claims, 14 Drawing Sheets

Related U.S. Application Data

(60) Provisional application No. 61/931,208, filed on Jan. 24, 2014.

(56) References Cited

U.S. PATENT DOCUMENTS

| | | |
|---|---|---|
| 4,423,730 A | 1/1984 | Gabbay |
| 4,491,986 A | 1/1985 | Gabbay |
| 4,759,758 A | 7/1988 | Gabbay |
| 4,816,029 A | 3/1989 | Penny, III et al. |
| 4,878,906 A | 11/1989 | Lindemann et al. |
| 4,922,905 A | 5/1990 | Strecker |
| 4,994,077 A | 2/1991 | Dobben |
| 5,411,552 A | 5/1995 | Andersen et al. |
| 5,415,664 A | 5/1995 | Pinchuk |
| 5,480,423 A | 1/1996 | Ravenscroft et al. |
| 5,843,167 A | 12/1998 | Dwyer et al. |
| 5,855,601 A | 1/1999 | Bessler et al. |
| 5,924,424 A | 7/1999 | Stevens et al. |
| 5,935,163 A | 8/1999 | Gabbay |
| 5,961,549 A | 10/1999 | Nguyen et al. |
| 5,968,068 A | 10/1999 | Dehdashtian et al. |
| 6,045,576 A | 4/2000 | Starr et al. |
| 6,077,297 A | 6/2000 | Robinson et al. |
| 6,083,257 A | 7/2000 | Taylor et al. |
| 6,090,140 A | 7/2000 | Gabbay |
| 6,214,036 B1 | 4/2001 | Letendre et al. |
| 6,264,691 B1 | 7/2001 | Gabbay |
| 6,267,783 B1 | 7/2001 | Letendre et al. |
| 6,306,141 B1 | 10/2001 | Jervis |
| 6,368,348 B1 | 4/2002 | Gabbay |
| 6,419,695 B1 | 7/2002 | Gabbay |
| 6,458,153 B1 | 10/2002 | Bailey et al. |
| 6,468,660 B2 | 10/2002 | Ogle et al. |
| 6,488,702 B1 | 12/2002 | Besselink |
| 6,517,576 B2 | 2/2003 | Gabbay |
| 6,533,810 B2 | 3/2003 | Hankh et al. |
| 6,582,464 B2 | 6/2003 | Gabbay |
| 6,610,088 B1 | 8/2003 | Gabbay |
| 6,623,518 B2 | 9/2003 | Thompson et al. |
| 6,652,578 B2 | 11/2003 | Bailey et al. |
| 6,685,625 B2 | 2/2004 | Gabbay |
| 6,716,244 B2 | 4/2004 | Klaco |
| 6,719,789 B2 | 4/2004 | Cox |
| 6,730,118 B2 | 5/2004 | Spenser et al. |
| 6,783,556 B1 | 8/2004 | Gabbay |
| 6,790,230 B2 | 9/2004 | Beyersdorf et al. |
| 6,814,746 B2 | 11/2004 | Thompson et al. |
| 6,830,584 B1 | 12/2004 | Seguin |
| 6,869,444 B2 | 3/2005 | Gabbay |
| 6,893,460 B2 | 5/2005 | Spenser et al. |
| 6,908,481 B2 | 6/2005 | Cribier |
| 6,951,573 B1 | 10/2005 | Dilling |
| 7,018,406 B2 | 3/2006 | Seguin et al. |
| 7,025,780 B2 | 4/2006 | Gabbay |
| 7,137,184 B2 | 11/2006 | Schreck |
| 7,160,322 B2 | 1/2007 | Gabbay |
| 7,195,641 B2 | 3/2007 | Palmaz et al. |
| 7,247,167 B2 | 7/2007 | Gabbay |
| 7,267,686 B2 | 9/2007 | DiMatteo et al. |
| 7,276,078 B2 | 10/2007 | Spenser et al. |
| 7,311,730 B2 | 12/2007 | Gabbay |
| 7,320,704 B2 | 1/2008 | Lashinski et al. |
| 7,329,278 B2 | 2/2008 | Seguin et al. |
| 7,374,573 B2 | 5/2008 | Gabbay |
| 7,381,218 B2 | 6/2008 | Schreck |
| 7,381,219 B2 | 6/2008 | Salahieh et al. |
| 7,452,371 B2 | 11/2008 | Pavcnik et al. |
| 7,510,572 B2 | 3/2009 | Gabbay |
| 7,510,575 B2 | 3/2009 | Spenser et al. |
| 7,524,331 B2 | 4/2009 | Birdsall |
| 7,534,261 B2 | 5/2009 | Friedman |
| RE40,816 E | 6/2009 | Taylor et al. |
| 7,585,321 B2 | 9/2009 | Cribier |
| 7,628,805 B2 | 12/2009 | Spenser et al. |
| 7,682,390 B2 | 3/2010 | Seguin |
| 7,708,775 B2 | 5/2010 | Rowe et al. |
| 7,731,742 B2 | 6/2010 | Schlick et al. |
| 7,748,389 B2 | 7/2010 | Salahieh et al. |
| 7,780,725 B2 | 8/2010 | Haug et al. |
| 7,799,069 B2 | 9/2010 | Bailey et al. |
| 7,803,185 B2 | 9/2010 | Gabbay |
| 7,824,442 B2 | 11/2010 | Salahieh et al. |
| 7,837,727 B2 | 11/2010 | Goetz et al. |
| 7,846,203 B2 | 12/2010 | Cribier |
| 7,846,204 B2 | 12/2010 | Letac et al. |
| 7,857,845 B2 | 12/2010 | Stacchino et al. |
| 7,892,281 B2 | 2/2011 | Seguin et al. |
| 7,914,569 B2 | 3/2011 | Nguyen et al. |
| 7,959,666 B2 | 6/2011 | Salahieh et al. |
| 7,959,672 B2 | 6/2011 | Salahieh et al. |
| 7,972,378 B2 | 7/2011 | Tabor et al. |
| 7,988,724 B2 | 8/2011 | Salahieh et al. |
| 7,993,394 B2 | 8/2011 | Hariton et al. |
| 8,016,877 B2 | 9/2011 | Seguin et al. |
| D648,854 S | 11/2011 | Braido |
| 8,048,153 B2 | 11/2011 | Salahieh et al. |
| 8,052,741 B2 | 11/2011 | Bruszewski et al. |
| 8,052,749 B2 | 11/2011 | Salahieh et al. |
| 8,052,750 B2 | 11/2011 | Tuval et al. |
| 8,062,355 B2 | 11/2011 | Figulla et al. |
| 8,075,611 B2 | 12/2011 | Millwee et al. |
| D652,926 S | 1/2012 | Braido |
| D652,927 S | 1/2012 | Braido et al. |
| D653,341 S | 1/2012 | Braido et al. |
| D653,342 S | 1/2012 | Braido et al. |
| D653,343 S | 1/2012 | Ness et al. |
| D654,169 S | 2/2012 | Braido |
| D654,170 S | 2/2012 | Braido et al. |
| 8,137,398 B2 | 3/2012 | Tuval et al. |
| 8,142,497 B2 | 3/2012 | Friedman |
| D660,432 S | 5/2012 | Braido |
| D660,433 S * | 5/2012 | Braido ............ A61F 2/91 D24/155 |
| D660,967 S | 5/2012 | Braido et al. |
| 8,182,528 B2 | 5/2012 | Salahieh et al. |
| 8,221,493 B2 | 7/2012 | Boyle et al. |
| 8,230,717 B2 | 7/2012 | Matonick |
| 8,231,670 B2 | 7/2012 | Salahieh et al. |
| 8,252,051 B2 | 8/2012 | Chau et al. |
| 8,308,798 B2 | 11/2012 | Pintor et al. |
| 8,313,525 B2 | 11/2012 | Tuval et al. |
| 8,323,335 B2 | 12/2012 | Rowe et al. |
| 8,323,336 B2 | 12/2012 | Hill et al. |
| 8,343,213 B2 | 1/2013 | Salahieh et al. |
| 8,348,995 B2 | 1/2013 | Tuval et al. |
| 8,348,996 B2 | 1/2013 | Tuval et al. |
| 8,348,998 B2 | 1/2013 | Pintor et al. |
| 8,366,769 B2 | 2/2013 | Huynh et al. |
| 8,403,983 B2 | 3/2013 | Quadri et al. |
| 8,408,214 B2 | 4/2013 | Spenser |
| 8,414,643 B2 | 4/2013 | Tuval et al. |
| 8,425,593 B2 | 4/2013 | Braido et al. |
| 8,449,599 B2 | 5/2013 | Chau et al. |
| 8,449,604 B2 | 5/2013 | Moaddeb et al. |
| D684,692 S | 6/2013 | Braido |
| 8,454,686 B2 | 6/2013 | Alkhatib |
| 8,500,798 B2 | 8/2013 | Rowe et al. |
| 8,568,474 B2 | 10/2013 | Yeung et al. |
| 8,579,962 B2 | 11/2013 | Salahieh et al. |
| 8,579,966 B2 | 11/2013 | Seguin et al. |
| 8,585,755 B2 | 11/2013 | Chau et al. |
| 8,591,575 B2 | 11/2013 | Cribier |
| 8,597,349 B2 | 12/2013 | Alkhatib |
| 8,603,159 B2 | 12/2013 | Seguin et al. |
| 8,603,160 B2 | 12/2013 | Salahieh et al. |
| 8,613,765 B2 | 12/2013 | Bonhoeffer et al. |
| 8,623,074 B2 | 1/2014 | Ryan |
| 8,652,204 B2 | 2/2014 | Quill et al. |
| 8,663,322 B2 | 3/2014 | Keranen |
| 8,668,733 B2 | 3/2014 | Haug et al. |
| 8,685,080 B2 | 4/2014 | White |
| 8,728,154 B2 | 5/2014 | Alkhatib |
| 8,747,459 B2 | 6/2014 | Nguyen et al. |
| 8,764,820 B2 | 7/2014 | Dehdashtian et al. |

(56) References Cited

U.S. PATENT DOCUMENTS

| | | |
|---|---|---|
| 8,795,357 B2 | 8/2014 | Yohanan et al. |
| 8,801,776 B2 | 8/2014 | House et al. |
| 8,808,356 B2 | 8/2014 | Braido et al. |
| 8,828,078 B2 | 9/2014 | Salahieh et al. |
| 8,834,563 B2 | 9/2014 | Righini |
| 8,840,661 B2 | 9/2014 | Manasse |
| 8,840,663 B2 | 9/2014 | Salahieh et al. |
| 8,876,894 B2 | 11/2014 | Tuval et al. |
| 8,876,895 B2 | 11/2014 | Tuval et al. |
| 8,940,040 B2 | 1/2015 | Shahriari |
| 8,945,209 B2 | 2/2015 | Bonyuet et al. |
| 8,961,595 B2 | 2/2015 | Alkhatib |
| 8,974,523 B2 | 3/2015 | Thill et al. |
| 8,974,524 B2 | 3/2015 | Yeung et al. |
| 9,326,856 B2 | 5/2016 | Schraut et al. |
| 9,820,852 B2 | 11/2017 | Braido et al. |
| 9,889,004 B2 | 2/2018 | Braido |
| 2002/0036220 A1 | 3/2002 | Gabbay |
| 2003/0014104 A1 | 1/2003 | Cribier |
| 2003/0023303 A1 | 1/2003 | Palmaz et al. |
| 2003/0040792 A1 | 2/2003 | Gabbay |
| 2003/0050694 A1 | 3/2003 | Yang et al. |
| 2003/0130726 A1 | 7/2003 | Thorpe et al. |
| 2004/0049262 A1 | 3/2004 | Obermiller et al. |
| 2004/0093075 A1 | 5/2004 | Kuehne |
| 2004/0111111 A1 | 6/2004 | Lin |
| 2004/0186563 A1 | 9/2004 | Lobbi |
| 2004/0210304 A1 | 10/2004 | Seguin et al. |
| 2004/0260389 A1 | 12/2004 | Case et al. |
| 2005/0075720 A1* | 4/2005 | Nguyen ............... A61F 2/243 623/1.26 |
| 2005/0096726 A1 | 5/2005 | Sequin et al. |
| 2005/0137682 A1 | 6/2005 | Justino |
| 2005/0137687 A1 | 6/2005 | Salahieh et al. |
| 2005/0137695 A1 | 6/2005 | Salahieh et al. |
| 2005/0137697 A1 | 6/2005 | Salahieh et al. |
| 2005/0137701 A1 | 6/2005 | Salahieh et al. |
| 2005/0203605 A1 | 9/2005 | Dolan |
| 2005/0240200 A1 | 10/2005 | Bergheim |
| 2005/0256566 A1 | 11/2005 | Gabbay |
| 2006/0008497 A1 | 1/2006 | Gabbay |
| 2006/0074484 A1 | 4/2006 | Huber |
| 2006/0106415 A1 | 5/2006 | Gabbay |
| 2006/0122692 A1 | 6/2006 | Gilad et al. |
| 2006/0142848 A1 | 6/2006 | Gabbay |
| 2006/0149360 A1 | 7/2006 | Schwammenthal et al. |
| 2006/0161249 A1 | 7/2006 | Realyvasquez et al. |
| 2006/0167468 A1 | 7/2006 | Gabbay |
| 2006/0173532 A1 | 8/2006 | Flagle et al. |
| 2006/0178740 A1 | 8/2006 | Stacchino et al. |
| 2006/0195180 A1 | 8/2006 | Kheradvar et al. |
| 2006/0206202 A1 | 9/2006 | Bonhoeffer et al. |
| 2006/0241744 A1 | 10/2006 | Beith |
| 2006/0241745 A1 | 10/2006 | Solem |
| 2006/0259120 A1 | 11/2006 | Vongphakdy et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0276813 A1 | 12/2006 | Greenberg |
| 2006/0276874 A1 | 12/2006 | Wilson et al. |
| 2006/0287717 A1 | 12/2006 | Rowe et al. |
| 2007/0010876 A1 | 1/2007 | Salahieh et al. |
| 2007/0016285 A1 | 1/2007 | Lane et al. |
| 2007/0027534 A1 | 2/2007 | Bergheim et al. |
| 2007/0043431 A1 | 2/2007 | Melsheimer |
| 2007/0043435 A1 | 2/2007 | Seguin et al. |
| 2007/0055358 A1 | 3/2007 | Krolik et al. |
| 2007/0067029 A1 | 3/2007 | Gabbay |
| 2007/0073387 A1 | 3/2007 | Forster et al. |
| 2007/0073391 A1 | 3/2007 | Bourang et al. |
| 2007/0088431 A1 | 4/2007 | Bourang et al. |
| 2007/0093890 A1 | 4/2007 | Eliasen et al. |
| 2007/0100435 A1 | 5/2007 | Case et al. |
| 2007/0112422 A1 | 5/2007 | Dehdashtian |
| 2007/0118210 A1 | 5/2007 | Pinchuk |
| 2007/0162100 A1 | 7/2007 | Gabbay |
| 2007/0168013 A1 | 7/2007 | Douglas |
| 2007/0203575 A1 | 8/2007 | Forster et al. |
| 2007/0213813 A1 | 9/2007 | Von Segesser et al. |
| 2007/0233228 A1 | 10/2007 | Eberhardt et al. |
| 2007/0239271 A1 | 10/2007 | Nguyen |
| 2007/0244545 A1 | 10/2007 | Birdsall et al. |
| 2007/0244552 A1 | 10/2007 | Salahieh et al. |
| 2007/0288087 A1 | 12/2007 | Feamot et al. |
| 2008/0021552 A1 | 1/2008 | Gabbay |
| 2008/0039934 A1 | 2/2008 | Styrc |
| 2008/0071369 A1 | 3/2008 | Tuval et al. |
| 2008/0082164 A1 | 4/2008 | Friedman |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147182 A1 | 6/2008 | Righini et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0243245 A1 | 10/2008 | Thambar et al. |
| 2008/0255662 A1 | 10/2008 | Stacchino et al. |
| 2008/0262602 A1 | 10/2008 | Wilk et al. |
| 2008/0269879 A1 | 10/2008 | Sathe et al. |
| 2009/0054975 A1 | 2/2009 | del Nido et al. |
| 2009/0099653 A1 | 4/2009 | Suri et al. |
| 2009/0112309 A1 | 4/2009 | Jaramillo et al. |
| 2009/0138079 A1 | 5/2009 | Tuval et al. |
| 2009/0276027 A1 | 11/2009 | Glynn |
| 2009/0276040 A1 | 11/2009 | Rowe et al. |
| 2009/0287299 A1 | 11/2009 | Tabor et al. |
| 2010/0004740 A1 | 1/2010 | Seguin et al. |
| 2010/0036484 A1 | 2/2010 | Hariton et al. |
| 2010/0049306 A1 | 2/2010 | House et al. |
| 2010/0082094 A1 | 4/2010 | Quadri et al. |
| 2010/0087907 A1 | 4/2010 | Lattouf |
| 2010/0131055 A1 | 5/2010 | Case et al. |
| 2010/0168778 A1 | 7/2010 | Braido |
| 2010/0168839 A1 | 7/2010 | Braido et al. |
| 2010/0168844 A1 | 7/2010 | Toomes et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0234940 A1 | 9/2010 | Dolan |
| 2010/0249911 A1 | 9/2010 | Alkhatib |
| 2010/0249923 A1 | 9/2010 | Alkhatib et al. |
| 2010/0286768 A1 | 11/2010 | Alkhatib |
| 2010/0298931 A1 | 11/2010 | Quadri et al. |
| 2011/0029072 A1 | 2/2011 | Gabbay |
| 2011/0054466 A1 | 3/2011 | Rothstein et al. |
| 2011/0098800 A1 | 4/2011 | Braido et al. |
| 2011/0098802 A1 | 4/2011 | Braido et al. |
| 2011/0137397 A1 | 6/2011 | Chau et al. |
| 2011/0172765 A1 | 7/2011 | Nguyen et al. |
| 2011/0208283 A1 | 8/2011 | Rust |
| 2011/0224678 A1 | 9/2011 | Gabbay |
| 2011/0238168 A1 | 9/2011 | Pellegrini et al. |
| 2011/0264206 A1 | 10/2011 | Tabor |
| 2011/0295363 A1 | 12/2011 | Girard et al. |
| 2012/0035722 A1 | 2/2012 | Tuval |
| 2012/0041550 A1 | 2/2012 | Salahieh et al. |
| 2012/0053681 A1 | 3/2012 | Alkhatib et al. |
| 2012/0071969 A1 | 3/2012 | Li et al. |
| 2012/0078347 A1 | 3/2012 | Braido et al. |
| 2012/0078350 A1 | 3/2012 | Wang et al. |
| 2012/0101572 A1 | 4/2012 | Kovalsky et al. |
| 2012/0123529 A1 | 5/2012 | Levi et al. |
| 2012/0143324 A1 | 6/2012 | Rankin et al. |
| 2012/0303116 A1 | 11/2012 | Gorman, III et al. |
| 2013/0018458 A1 | 1/2013 | Yohanan et al. |
| 2013/0274873 A1 | 10/2013 | Delaloye et al. |
| 2013/0304200 A1 | 11/2013 | McLean et al. |
| 2013/0331929 A1 | 12/2013 | Mitra et al. |
| 2014/0005771 A1 | 1/2014 | Braido et al. |
| 2014/0121763 A1 | 5/2014 | Duffy et al. |
| 2014/0155997 A1 | 6/2014 | Braido |

(56) References Cited

U.S. PATENT DOCUMENTS

| | | |
|---|---|---|
| 2014/0214159 A1 | 7/2014 | Vidlund et al. |
| 2014/0228946 A1 | 8/2014 | Chau et al. |
| 2014/0303719 A1 | 10/2014 | Cox et al. |
| 2014/0324164 A1 | 10/2014 | Gross et al. |
| 2014/0343671 A1 | 11/2014 | Yohanan et al. |
| 2014/0350668 A1 | 11/2014 | Delaloye et al. |
| 2014/0350669 A1 | 11/2014 | Gillespie et al. |

FOREIGN PATENT DOCUMENTS

| | | |
|---|---|---|
| DE | 102005003632 A1 | 8/2006 |
| EP | 0850607 A1 | 7/1998 |
| EP | 1000590 A1 | 5/2000 |
| EP | 1584306 A1 | 10/2005 |
| EP | 1598031 A2 | 11/2005 |
| EP | 1360942 B1 | 12/2005 |
| EP | 1926455 A2 | 6/2008 |
| EP | 2537487 A1 | 12/2012 |
| EP | 2870946 A1 | 5/2015 |
| EP | 2898859 A1 | 7/2015 |
| EP | 2898859 B1 | 11/2018 |
| FR | 2850008 A1 | 7/2004 |
| FR | 2847800 B1 | 10/2005 |
| JE | 202008009610 U1 | 12/2008 |
| NO | 10008549 A1 | 1/2010 |
| NO | 10096176 A1 | 8/2010 |
| WO | 9117720 A1 | 11/1991 |
| WO | 9716133 A1 | 5/1997 |
| WO | 9832412 A2 | 7/1998 |
| WO | 9913801 A1 | 3/1999 |
| WO | 01028459 A1 | 4/2001 |
| WO | 0149213 A2 | 7/2001 |
| WO | 01054625 A1 | 8/2001 |
| WO | 01056500 A2 | 8/2001 |
| WO | 01076510 A2 | 10/2001 |
| WO | 0236048 A1 | 5/2002 |
| WO | 0247575 A2 | 6/2002 |
| WO | 02067782 A2 | 9/2002 |
| WO | 03047468 A1 | 6/2003 |
| WO | 2005062980 A2 | 7/2005 |
| WO | 2005070343 A1 | 8/2005 |
| WO | 06073626 A2 | 7/2006 |
| WO | 07071436 A2 | 6/2007 |
| WO | 08070797 A2 | 6/2008 |
| WO | 2009024859 A2 | 2/2009 |
| WO | 2009042196 A2 | 4/2009 |
| WO | 2010008548 A2 | 1/2010 |
| WO | 2010098857 A1 | 9/2010 |
| WO | 2011133787 A1 | 10/2011 |
| WO | 2012048035 A2 | 4/2012 |
| WO | 2012177942 A2 | 12/2012 |
| WO | 2013028387 A2 | 2/2013 |
| WO | 2014163704 A1 | 10/2014 |
| WO | 2014164149 | 10/2014 |
| WO | 2014164151 A1 | 10/2014 |
| WO | 2015077274 A1 | 5/2015 |

OTHER PUBLICATIONS

International Search Report and Written Opinion for Application No. PCT/US2015/011387 dated Mar. 30, 2015.

Extended European Search Report for Application No. 15152315.6 dated May 29, 2015.

Extended European Search Report for Application No. 15152324.8 dated Jun. 10, 2015.

Rohde, et al., "Resection of Calcified Aortic Heart Leaflets In Vitro by Q-Switched 2 μm Microsecond Laser Radiation", Journal of Cardiac Surgery, 30(2):157-62. Feb. 2015.

Muñoz, et al., "Guidance of treatment of perivalvular prosthetic leaks.", Current cardiology reports, 16.430, 6 pages, Jan. 2014.

Gössl, Mario, and Charanjit S. Rihal. "Percutaneous treatment of aortic and mitral valve paravalvular regurgitation." Current cardiology reports 15.8 (2013): 1-8.

Swiatkiewicz, Iwona, et al. "Percutaneous closure of mitral perivalvular leak." Kardiologia polska 67.7 (2009): 762.

De Cicco, Giuseppe, et al. "Aortic valve periprosthetic leakage: anatomic observations and surgical results." The Annals of thoracic surgery 79.5 (2005): 1480-1485.

Heat Advisor, "Heart repairs without surgery. Minimally invasive procedures aim to correct valve leakage", Sep. 2004, PubMed ID 15586429.

Transcatheter Umbrella Closure of Valvular and Paravalvular Leaks, Hourihan et al., Journal of the American College of Cardiology, vol. 20, No. 6, pp. 1371-1377, (1992).

Buellesfeld et al., Treatment of paravalvular leaks through inverventional techniques; Department of Cardiology, Ben University Hospital 2011.

Preliminary Opinion of the Opposition Division Indicating Issue of Summons to Follow at a Later Time and Shorter Notice for EP15152324.8 dated May 13, 2020; 12 pages.

Braido, Peter N., U.S. Appl. No. 61/931,265, filed Jan. 24, 2014; Stationary Intra-Annular Halo Designs for Paravalvular Leak (PVL) Reduction—Active Channel Filling Cuff Designs.

Ruiz, Carlos, Overview of PRE-CE Mark Transcatheter Aortic Valve Technologies, Euro PCR—dated May 25, 2010.

Percutaneous aortic valve replacement: resection before implantation, 836-840, Quaden, Rene et al., European J. of Cardio-thoracic Surgery, 27 (2005).

Catheter-implanted prosthetic heart valves, Knudsen, L.L., et al., The International Journal of Artificial Organs, vol. 16, No. 5 1993, pp. 253-262.

Transluminal Aortic Valve Placement, Moazami, Nader, et al., ASAIO Journal, 1996; 42:M381-M385.

Transluminal Catheter Implanted Prosthetic Heart Valves, Andersen, Henning Rud, International Journal of Angiology 7:102-106 (1998).

Transluminal implantation of artificial heart valves, Andersen, H. R., et al., European Heart Journal (1992) 13, 704-708.

Is It Reasonable to Treal All Calcified Stenotic Aortic Valves With a Valved Stent?, 579-584, Zegdi, Rachid, MD, PhD et al., J. of the American College of Cardiology, vol. 51, No. 5, Feb. 5, 2008.

"Direct-Access Valve Replacement", Christoph H. Huber, et al., Journal of the American College of Cardiology, vol. 46, No. 2, (Jul. 19, 2005).

"Percutaneous Aortic Valve Implantation Retrograde From the Femoral Artery", John G. Webb et al., Circulation, 2006; 113:842-850 (Feb. 6, 2006).

"Minimally invasive cardiac surgery", M. J. Mack, Surgical Endoscopy, 2006, 20:S488-S492, DOI: 10.1007/s00464-006-0110-8 (presented Apr. 24, 2006).

"Transapical Transcatheter Aortic Valve Implantation in Humans", Samuel V. Lichtenstein et al., Circulation. 2006; 114: 591-596 (Jul. 31, 2006).

"Transapical approach for sutureless stent-fixed aortic valve implantation: experimental results"; Th. Walther et al., European Journal of Cardio-thoracic Surgery 29 (2006) 703-708 (Jan. 30, 2006).

"Transapical aortic valve implantation: an animal feasibility study"; Todd M. Dewey et al., The annals of thoracic surgery 2006; 82: 110-6 (Feb. 13, 2006).

Textbook "Transcatheter Valve Repair", 2006, pp. 165-186.

\* cited by examiner

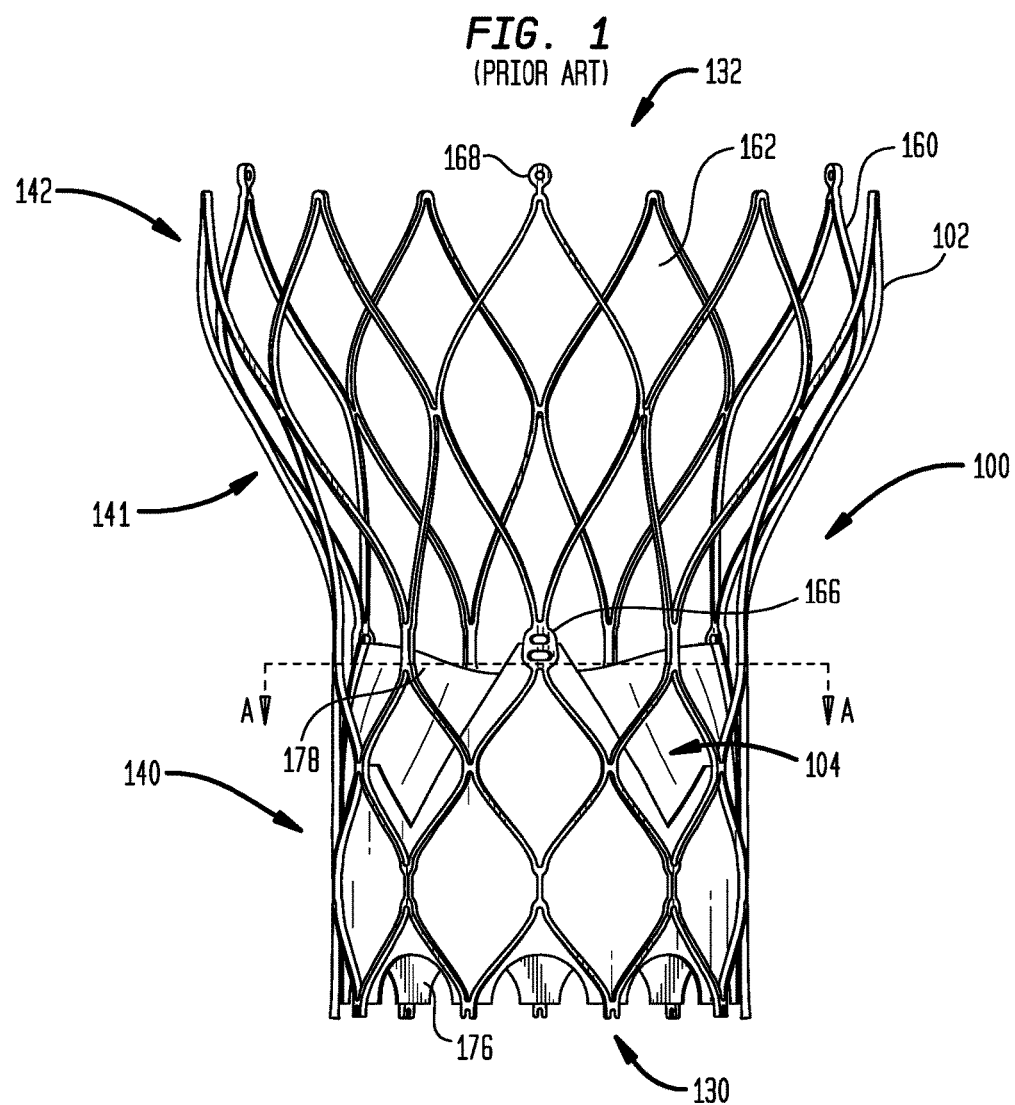
FIG. 1
(PRIOR ART)
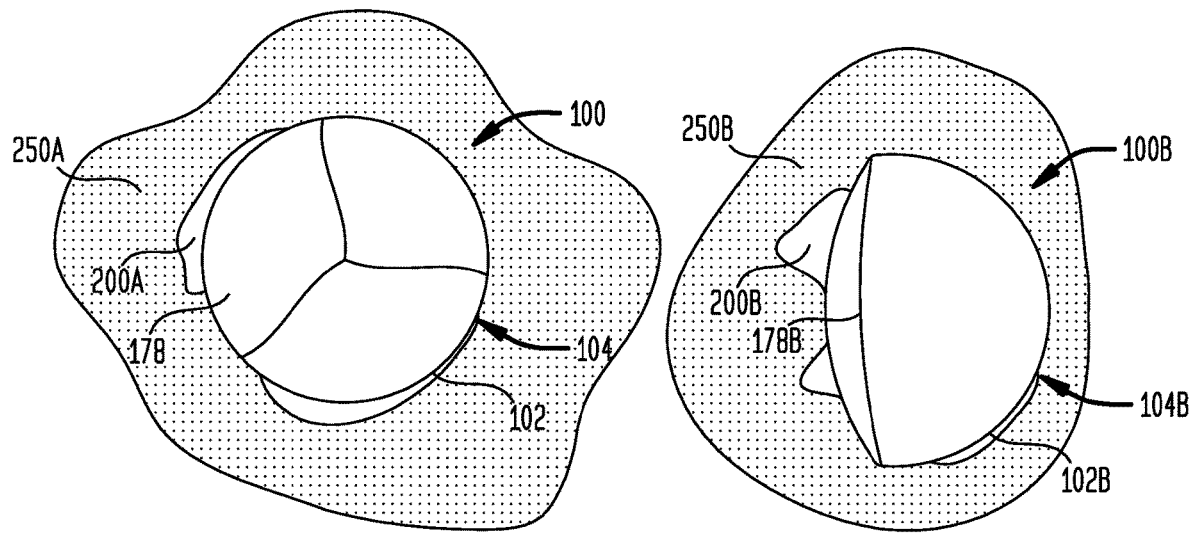
FIG. 2A
FIG. 2B

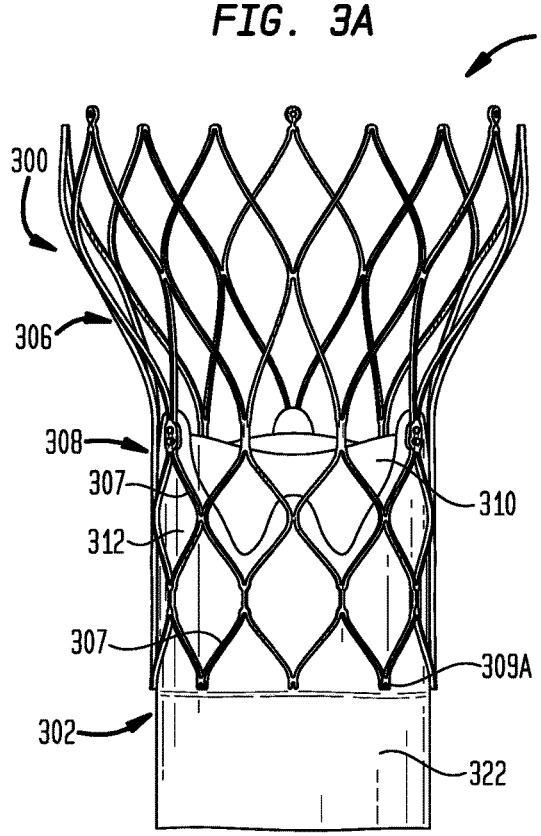
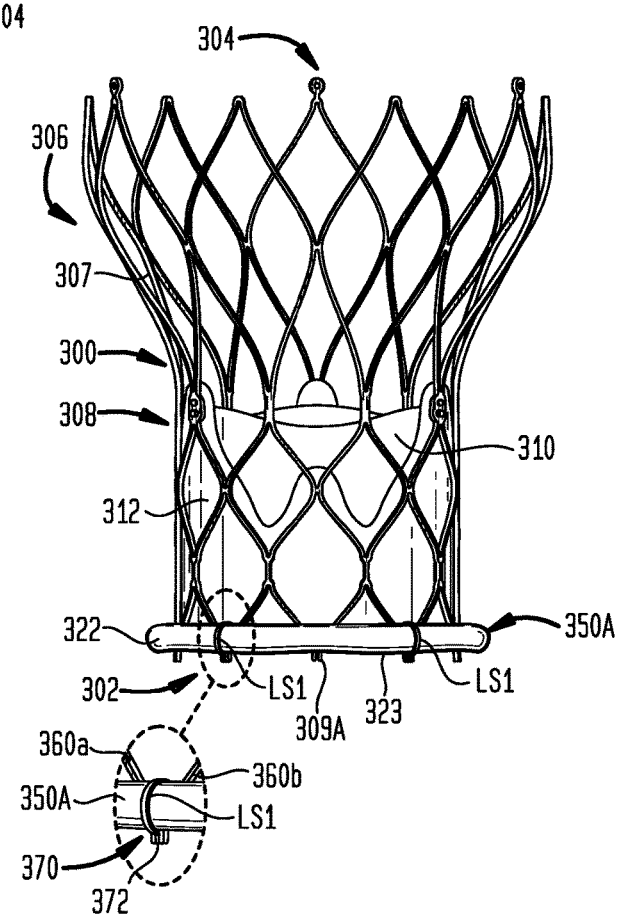
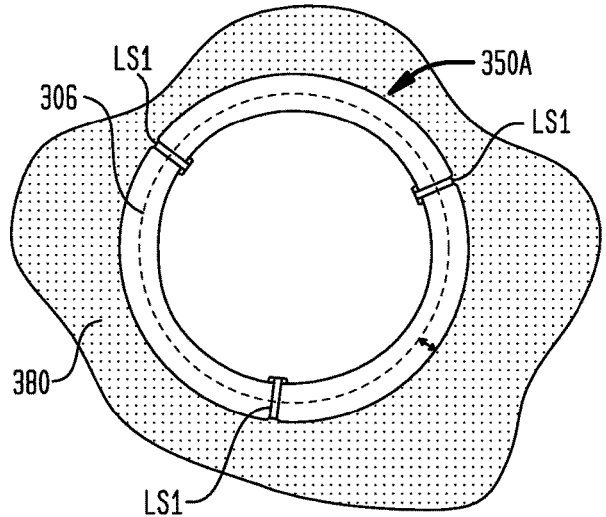
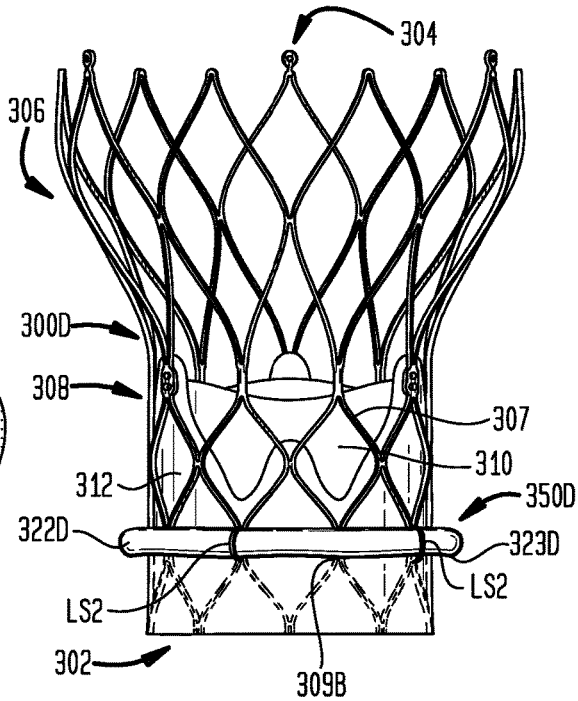

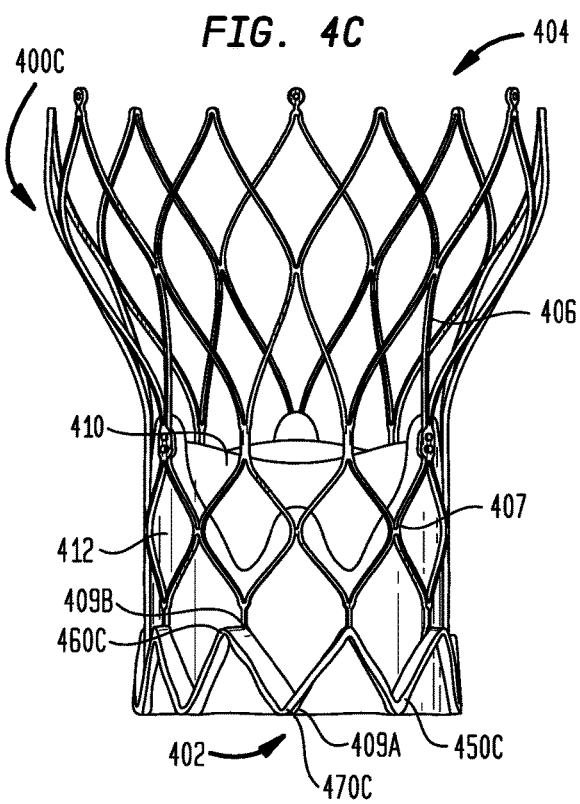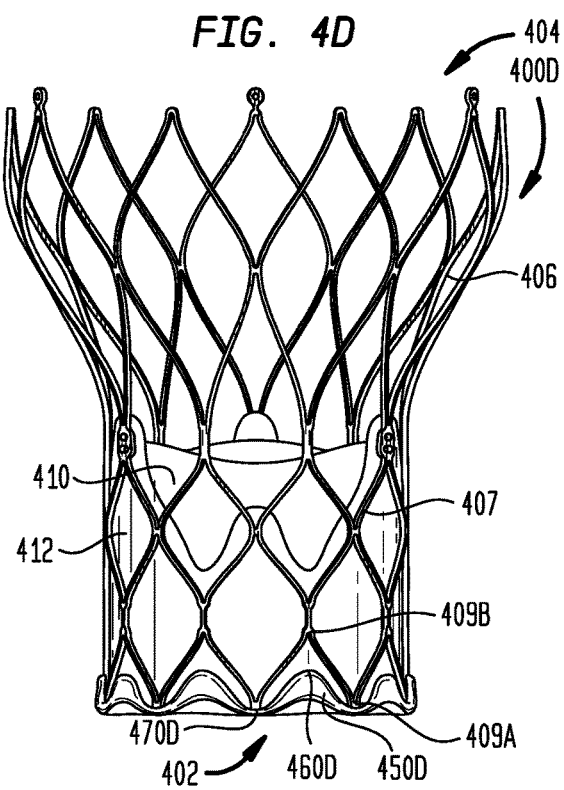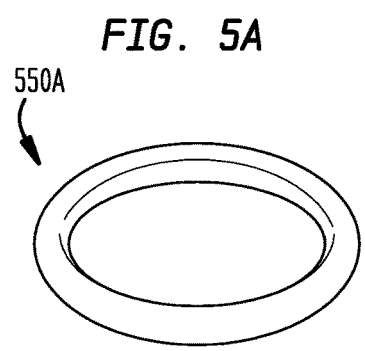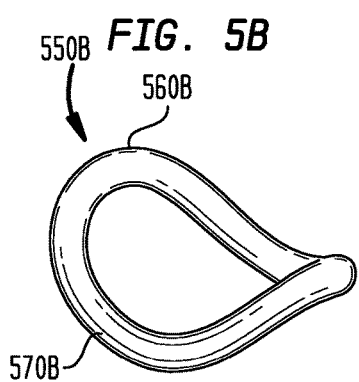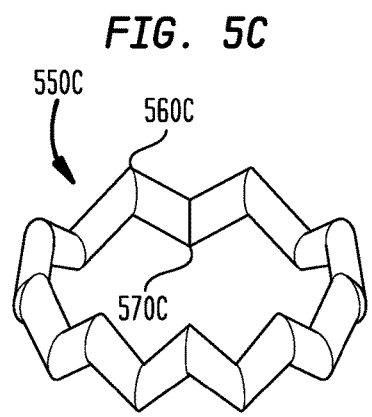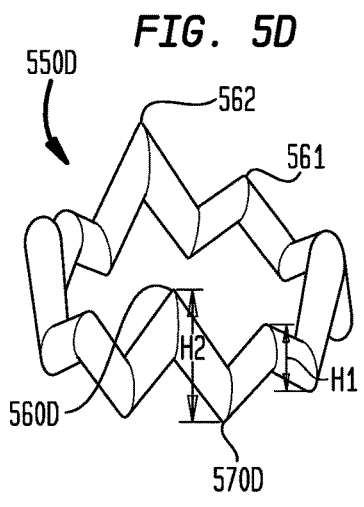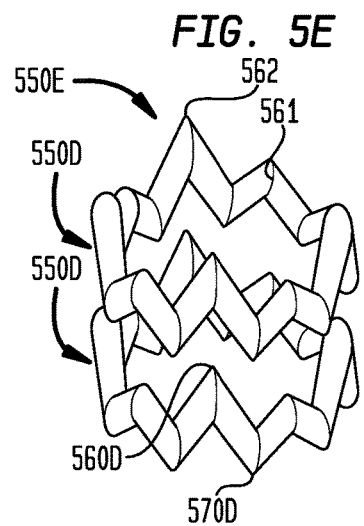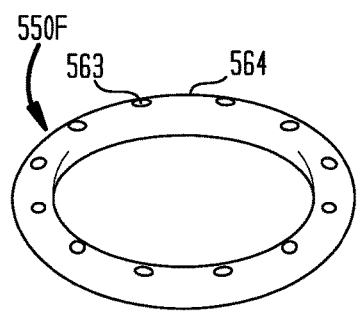

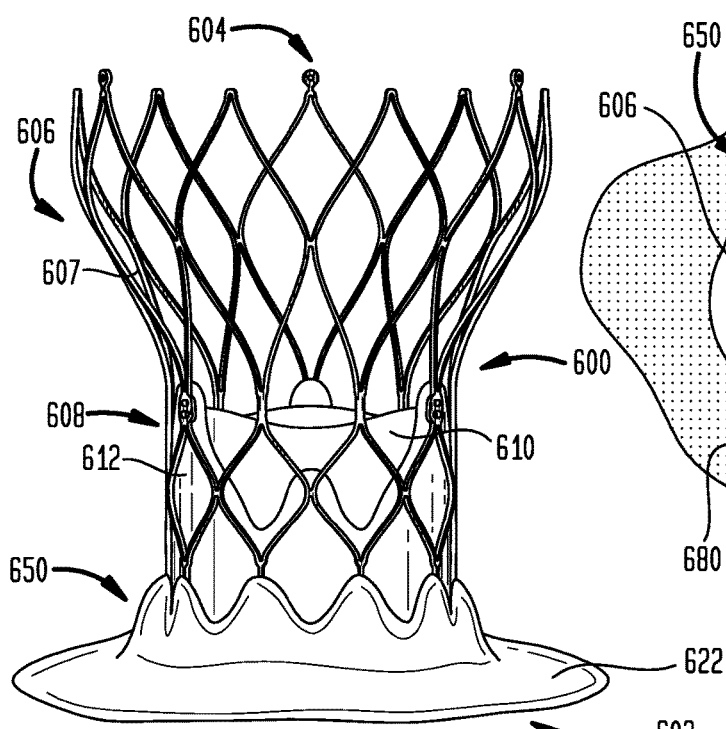
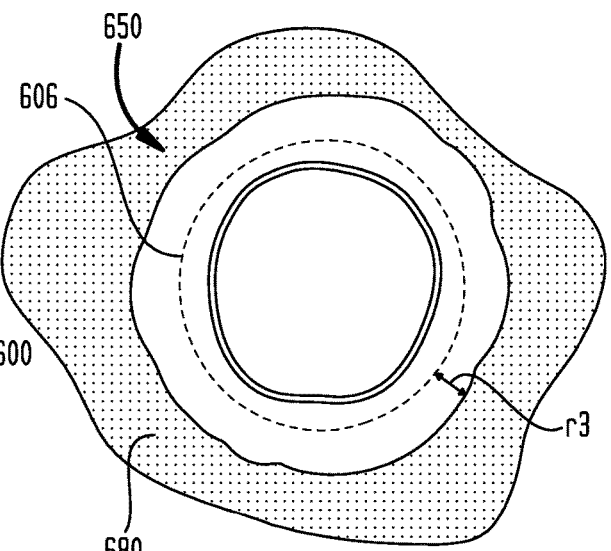
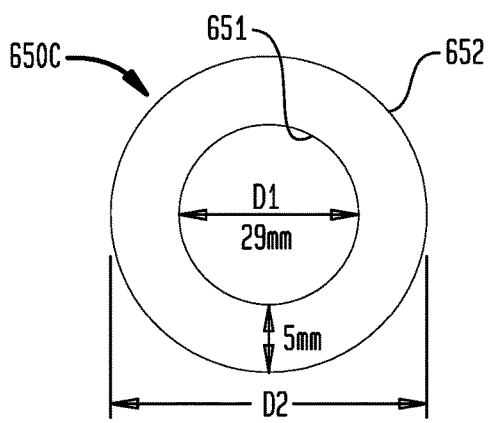
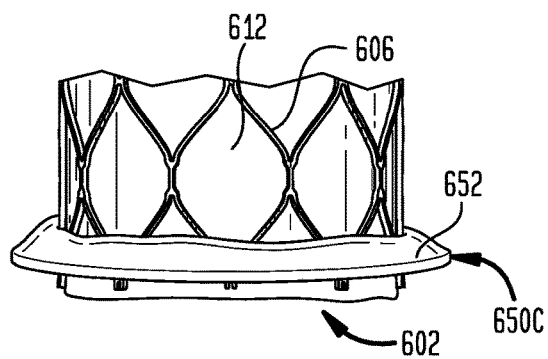
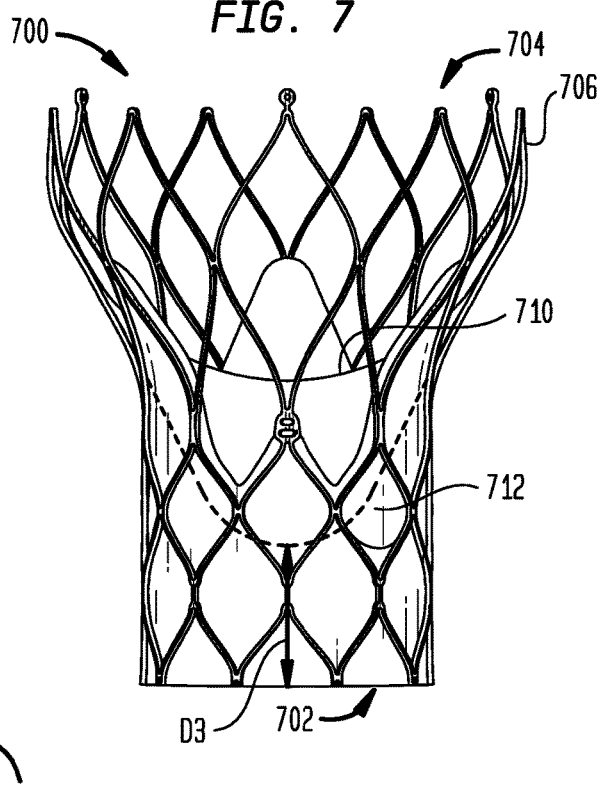

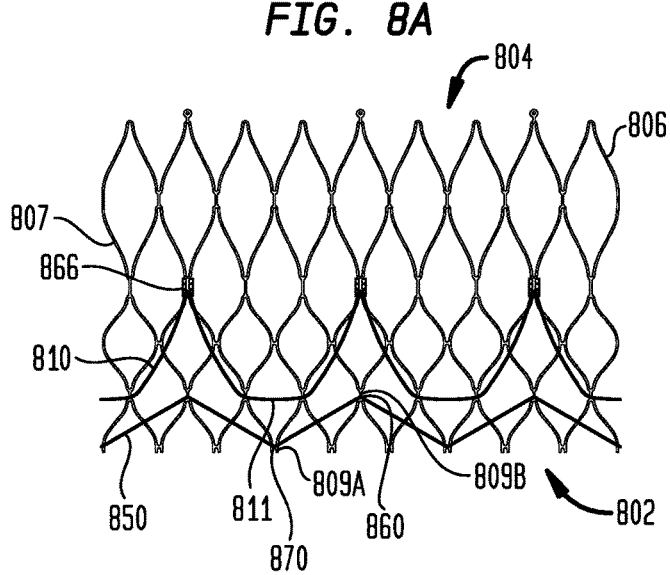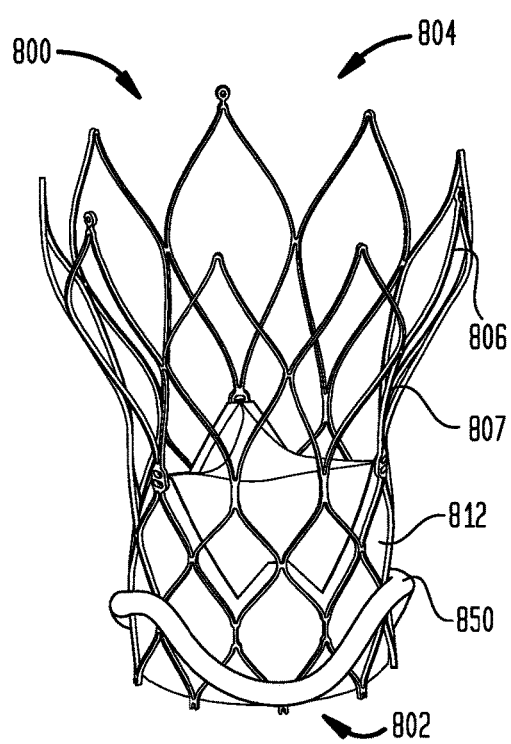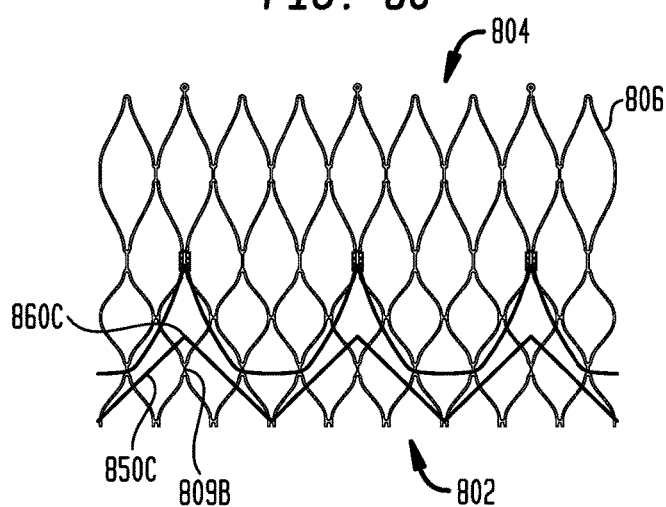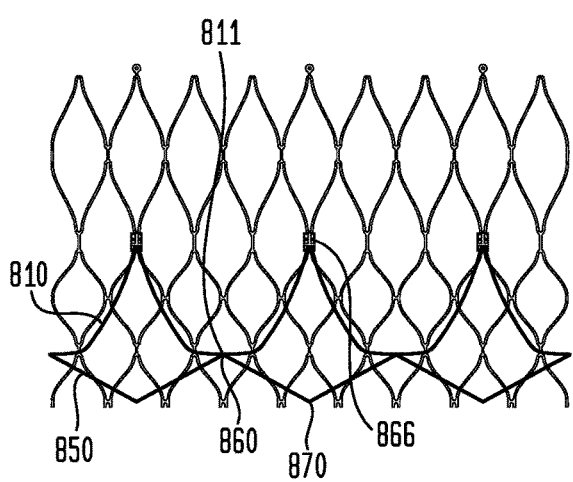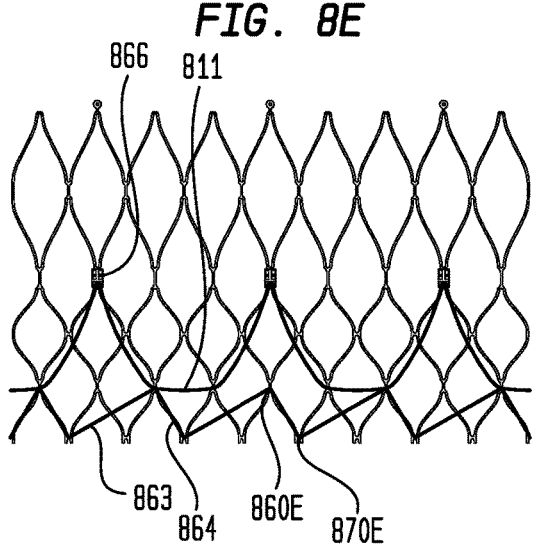

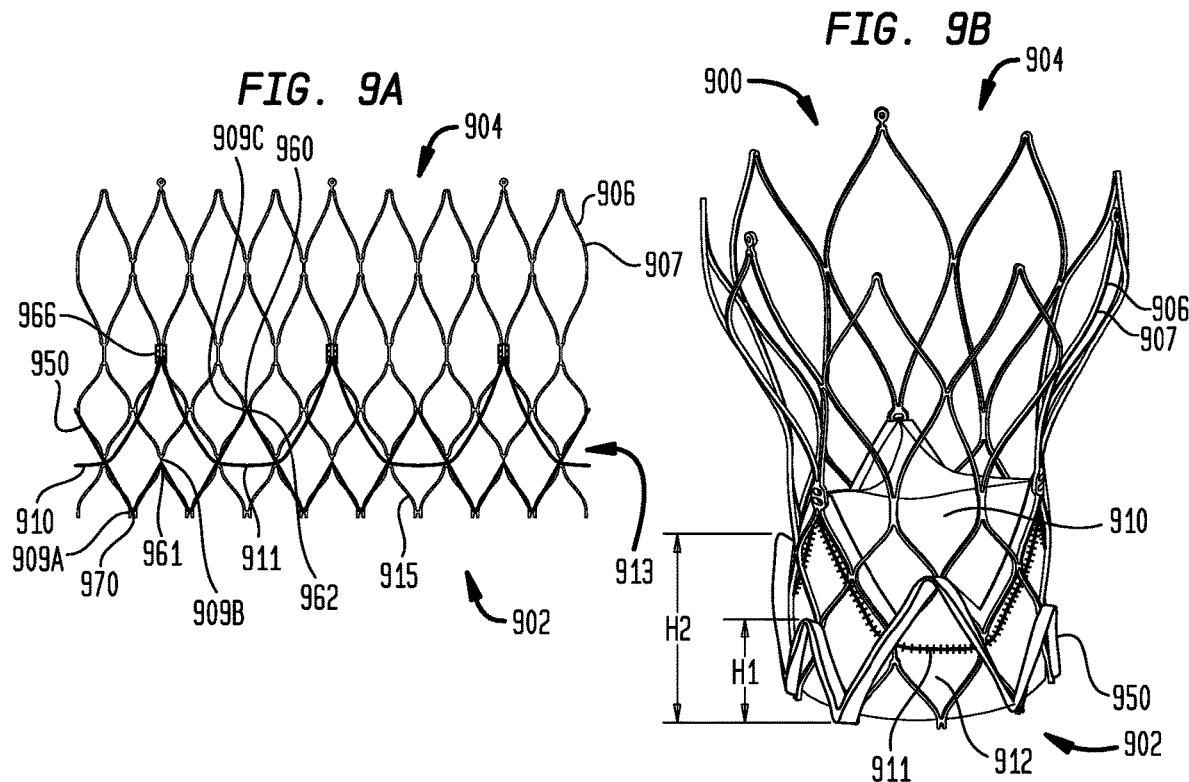
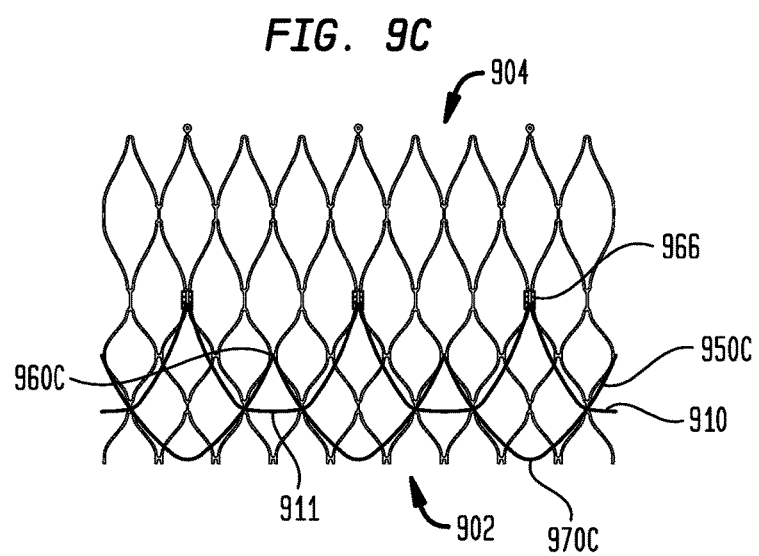

STATIONARY INTRA-ANNULAR HALO DESIGNS FOR PARAVALVULAR LEAK (PVL) REDUCTION-PASSIVE CHANNEL FILLING CUFF DESIGNS

CROSS-REFERENCE TO RELATED APPLICATION

The present application is a continuation of U.S. patent application Ser. No. 14/602,894 filed Jan. 22, 2015, which claims the benefit of the filing date of U.S. Provisional Patent Application No. 61/931,208 filed Jan. 24, 2014, the disclosures of which are hereby incorporated herein by reference.

BACKGROUND OF THE INVENTION

The present disclosure relates in general to heart valve replacement and, in particular, to collapsible prosthetic heart valves. More particularly, the present disclosure relates to devices and methods for positioning and sealing collapsible prosthetic heart valves within a native valve annulus.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two common types of stents on which the valve structures are ordinarily mounted: a self-expanding stent or a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, and then expanding a balloon positioned within the valve stent. For self-expanding valves, on the other hand, the stent automatically expands as the sheath covering the valve is withdrawn.

BRIEF SUMMARY OF THE INVENTION

Prosthetic heart valves and methods of expanding a prosthetic heart valve between native leaflets of a native aortic annulus of a patient are disclosed.

A prosthetic heart valve configured to be expanded between native leaflets of a native aortic annulus of a patient may include a collapsible and expandable stent extending in a flow direction between a proximal end and a distal end, a cuff attached to an annulus section of the stent, a plurality of prosthetic valve leaflets each having a belly attached to the cuff between a first location and a second location downstream of the first location in a flow direction, and a sealing structure attached to the annulus section of the stent.

The annulus section of the stent may be adjacent the proximal end. The stent may include a plurality of struts shaped to form a plurality of cells connected to one another in a plurality of annular rows around the stent. The flow direction may be defined from the proximal end toward the distal end. The sealing structure may have a deployed condition with a diameter greater than a diameter of the proximal end of the stent when the stent is in an expanded use condition.

The sealing structure may be entirely located between the proximal end of the stent and the first location. The sealing structure may be located partially between the proximal end of the stent the first location, and partially between the first location and the second location. The prosthetic heart valve may also include an underwire supporting a portion of the cuff and extending in a circumferential direction about a perimeter of the stent along locations where the bellies of the leaflets are attached to the cuff. The sealing structure may be attached to the stent and the cuff along the underwire. The underwire may be located within an interior of the sealing structure.

The sealing structure may extend continuously around a circumference of the stent. The sealing structure may have a top surface facing the distal end of the stent, the top surface including a plurality of openings in fluid communication with an interior of the sealing structure. The sealing structure may have a saddle ring shape with at least two peaks and at least two valleys, the valleys being closer to the proximal end of the stent than the peaks.

The sealing structure may have a zigzag ring shape with at least three peaks and at least three valleys, the valleys being closer to the proximal end of the stent than the peaks. The peaks may include at least one low peak that extends to a first height above the valleys and at least one high peak that extends to a second height above the valleys, the second height being greater than the first height. The stent may include commissure features each located at a juncture of adjacent ones of the bellies of the leaflets, at least a portion of the belly of each leaflet being attached to one of the commissure features, and the peaks may be substantially aligned with the commissure features in the flow direction.

The stent may include commissure features each located at a juncture of adjacent ones of the bellies of the leaflets, at least a portion of the belly of each leaflet being attached to one of the commissure features. The valleys may be substantially aligned with the commissure features in the flow direction. At least one of the valleys may include a portion that extends in a direction orthogonal to the flow direction, the portion not being attached to the cuff and stent and being configured to be under tension when the stent is in the expanded use condition.

The stent may includes commissure features each located at a juncture of adjacent ones of the bellies of the leaflets, at least a portion of the belly of each leaflet being attached to one of the commissure features. The portion may be substantially aligned with the commissure features in the flow direction. The sealing structure may include at least one discontinuous ring portion extending circumferentially about at least a portion of a perimeter of the stent. The at least one discontinuous ring portion may have a high end and a low end that are vertically displaced from one another in the flow direction. The high end and the low end may be aligned in the flow direction with one another, such that an imaginary line extending in the flow direction intersects the high end and the low end.

The sealing structure may include at least two discontinuous ring portions each extending circumferentially about at least a portion of a perimeter of the stent. The high end may be an end of a first one of the discontinuous ring portions, and the low end may be an end of a second one of the discontinuous ring portions. The sealing structure may include a continuous ring structure and at least one discontinuous ring portion. The at least one discontinuous ring portion may be disposed between the distal end of the stent and the continuous ring structure.

The stent may include commissure features each located at a juncture of adjacent ones of the bellies of the leaflets, at least a portion of the belly of each leaflet being attached to one of the commissure features. Each discontinuous ring portion may be substantially aligned with a corresponding one of the commissure features in the flow direction. The sealing structure may include two continuous ring structures. Each of the continuous ring structures may extend completely around a circumference of the stent.

BRIEF DESCRIPTION OF THE DRAWINGS

Various embodiments of heart valves are disclosed herein with reference to the drawings, wherein:

FIG. 1 is a side elevational view of a conventional prosthetic heart valve;

FIG. 2A is a highly schematic cross-sectional view taken along line A-A of FIG. 1 and showing the prosthetic heart valve disposed within a native valve annulus;

FIG. 2B is a highly schematic cross-sectional view showing a prosthetic mitral valve disposed within a native valve annulus;

FIGS. 3A and 3B are highly schematic side views of another embodiment of a heart valve having a sealing ring intended to fill irregularities between the heart valve and the native valve annulus;

FIG. 3C is a schematic end view of the prosthetic heart valve of FIGS. 3A and 3B after formation of the sealing ring as seen from the annulus end toward the aortic end of the heart valve;

FIG. 3D is a highly schematic side view of a variation of the embodiment shown in FIGS. 3A-3C;

FIG. 4C is a side view of another embodiment of a heart valve having an undulating sealing ring intended to fill irregularities between the heart valve and the native valve annulus;

FIG. 4D is a side view of another embodiment of a heart valve having an undulating sealing ring intended to fill irregularities between the heart valve and the native valve annulus;

FIGS. 5A-5F are highly schematic perspective views of alternative sealing ring embodiments that can be used with the stent, cuff, and leaflets of FIG. 4C;

FIG. 6A is a highly schematic side view of another embodiment of a heart valve having a halo sealing ring intended to fill irregularities between the heart valve and the native valve annulus;

FIG. 6B is a schematic end view of the prosthetic heart valve of FIG. 6A after formation of the halo sealing ring as seen from the annulus end toward the aortic end of the heart valve;

FIG. 6C is a schematic end view an alternative sealing ring embodiment that can be used with the stent, cuff, and leaflets of FIG. 6A;

FIG. 6D is an enlarged partial side view of a heart valve having the sealing ring of FIG. 6C attached thereto;

FIG. 7 is a side view of another embodiment of a heart valve having a higher cuff height;

FIG. 8A is a developed view of the stent, sealing ring, and leaflets of another embodiment of a heart valve having a sealing ring intended to fill irregularities between the heart valve and the native valve annulus;

FIG. 8B is a side view of a heart valve having the stent, sealing ring, and leaflets of FIG. 8A;

FIGS. 8C-8E are developed views of variations of the stent, sealing ring, and leaflets of FIG. 8A;

FIG. 9A is a developed view of the stent, sealing ring, and leaflets of another embodiment of a heart valve having a sealing ring intended to fill irregularities between the heart valve and the native valve annulus;

FIG. 9B is a side view of a heart valve having the stent, sealing ring, and leaflets of FIG. 9A;

FIG. 9C is a developed view of a variation of the stent, sealing ring, and leaflets of FIG. 9A;

Figure 4A:
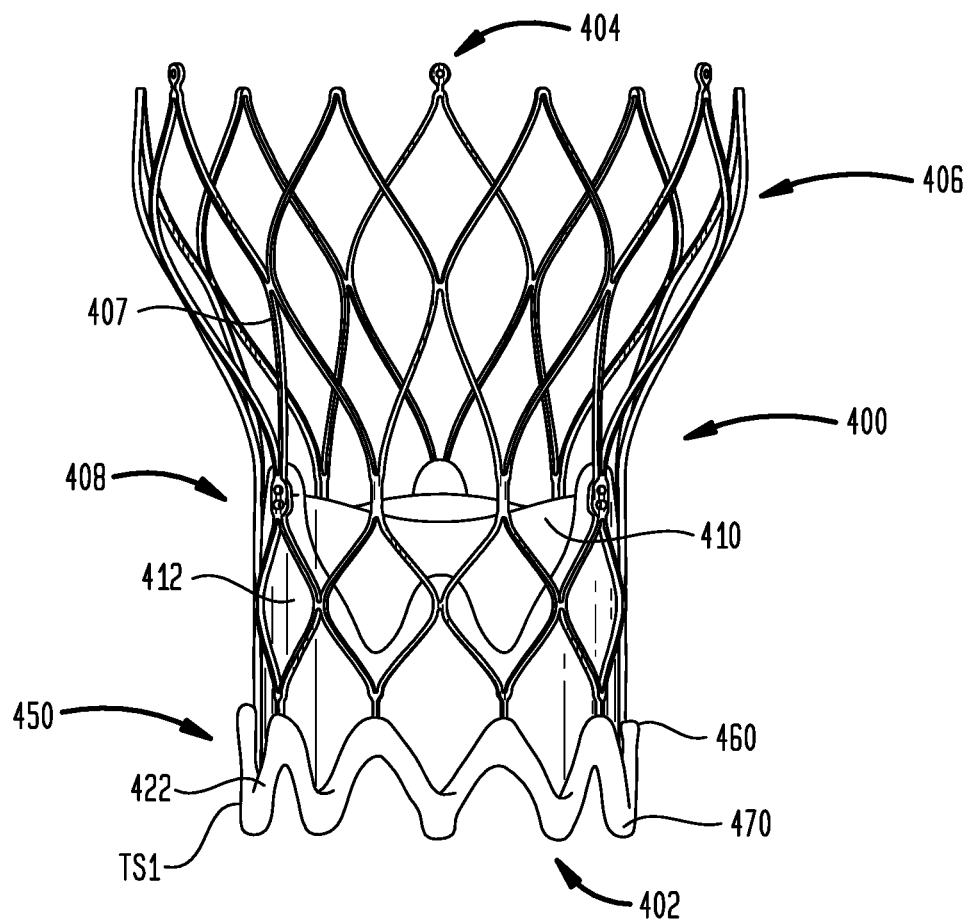
FIG. 4A is a highly schematic side view of another embodiment of a heart valve having an undulating sealing ring intended to fill irregularities between the heart valve and the native valve annulus.

Various embodiments of the present disclosure will now be described with reference to the appended drawings. It is to be appreciated that these drawings depict only some embodiments of the disclosure and are therefore not to be considered limiting of its scope.

DETAILED DESCRIPTION

With conventional self expanding valves, clinical success of the valve is dependent on accurate deployment and anchoring. Inaccurate deployment and anchoring of the valve increases risks, such as those associated with valve migration, which may cause severe complications and possibly death due to the obstruction of the left ventricular outflow tract. Inaccurate deployment and anchoring may also result in the leakage of blood between the implanted heart valve and the native valve annulus, commonly referred to as perivalvular leakage (also known as "paravalvular leakage"). In aortic valves, this leakage enables blood to flow from the aorta back into the left ventricle, reducing cardiac efficiency and putting a greater strain on the heart muscle. Additionally, calcification of the aortic valve may affect performance and the interaction between the implanted valve and the calcified tissue is believed to be relevant to leakage, as will be outlined below.

Moreover, anatomical variations from one patient to another may cause a fully deployed heart valve to function improperly, requiring removal of the valve from the patient. Removing a fully deployed heart valve increases the length of the procedure as well as the risk of infection and/or damage to heart tissue. Thus, methods and devices are desirable that would reduce the need to remove a prosthetic heart valve from a patient. Methods and devices are also desirable that would reduce the likelihood of perivalvular leakage due to gaps between the implanted heart valve and patient tissue.

As used herein, the term "proximal," when used in connection with a prosthetic heart valve, refers to the end of the heart valve closest to the heart when the heart valve is implanted in a patient, whereas the term "distal," when used in connection with a prosthetic heart valve, refers to the end of the heart valve farthest from the heart when the heart valve is implanted in a patient. When used in connection with devices for delivering a prosthetic heart valve or other medical device into a patient, the terms "trailing" and "leading" are to be taken as relative to the user of the delivery devices. "Trailing" is to be understood as relatively close to the user, and "leading" is to be understood as relatively farther away from the user. Also as used herein, the terms "generally," "substantially," "approximately," and "about" are intended to mean that slight deviations from absolute are included within the scope of the term so modified.

When used to indicate relative locations within the aortic annulus, the aortic root, and the ascending aorta of a patient, the terms "above" and "below" are to be taken as relative to the juncture between the aortic annulus and the left ventricle. "Above" is to be understood as relatively farther from the left ventricle, and "below" is to be understood as relatively closer to the left ventricle.

When used to indicate relative locations within the prosthetic heart valve, the terms "longitudinal" and "vertical" are to be taken as the direction of the axis extending between the proximal end and the distal end of the stent of the heart valve, along the direction of intended blood flow; the term "flow direction" is to be taken as the direction from the proximal end to the distal end of the stent of the heart valve, along the direction of intended blood flow; and the terms "above," "below," "high," and "low" are to be taken as relative to the proximal end of the stent. "Above" and "high" are to be understood as relatively farther from the proximal end of the stent in the flow direction toward the distal end of the stent, and "below" and "low" are to be understood as relatively closer to the proximal end of the stent in the flow direction. When used to indicate relative locations within the prosthetic heart valve, the term "circumferential" is to be taken as the direction of rotation about an axis extending in the flow direction of the stent.

The sealing portions of the present disclosure may be used in connection with collapsible prosthetic heart valves. FIG. 1 shows one such collapsible stent-supported prosthetic heart valve 100 including a stent 102 and a valve assembly 104 as is known in the art. The prosthetic heart valve 100 is designed to replace a native tricuspid valve of a patient, such as a native aortic valve. It should be noted that while the inventions herein are described predominantly in connection with their use with a prosthetic aortic valve and a stent having a shape as illustrated in FIG. 1, the valve could be a bicuspid valve, such as the mitral valve, and the stent could have different shapes, such as a flared or conical annulus section, a less-bulbous aortic section, and the like, and a differently shaped transition section.

The stent 102 may be formed from biocompatible materials that are capable of self-expansion, such as, for example, shape memory alloys, such as the nickel-titanium alloy known as "Nitinol" or other suitable metals or polymers. The stent 102 extends from a proximal or annulus end 130 to a distal or aortic end 132, and includes an annulus section 140 adjacent the proximal end 130, a transition section 141, and an aortic section 142 adjacent the distal end 132. The annulus section 140 has a relatively small cross-section in the expanded condition, while the aortic section 142 has a relatively large cross-section in the expanded condition. The annulus section 140 may be in the form of a cylinder having a substantially constant diameter along its length. The transition section 141 may taper outwardly from the annulus section 140 to the aortic section 142.

Each of the sections of the stent 102 includes a plurality of struts 160 forming cells 162 connected to one another in one or more annular rows around the stent. For example, as shown in FIG. 1, the annulus section 140 may have two annular rows of complete cells 162 and the aortic section 142 and the transition section 141 may each have one or more annular rows of partial cells 162. The cells 162 in the aortic section 142 may be larger than the cells 162 in the annulus section 140. The larger cells in the aortic section 142 better enable the prosthetic valve 100 to be positioned in the native valve annulus without the stent structure interfering with blood flow to the coronary arteries.

The stent 102 may include one or more retaining elements 168 at the distal end 132 thereof, the retaining elements 168 being sized and shaped to cooperate with female retaining structures (not shown) provided on the deployment device. The engagement of the retaining elements 168 with the female retaining structures on the deployment device helps maintain the prosthetic heart valve 100 in assembled relationship with the deployment device, minimizes longitudinal movement of the prosthetic heart valve relative to the deployment device during unsheathing or resheathing procedures, and helps prevent rotation of the prosthetic heart valve relative to the deployment device as the deployment device is advanced to the target location and the heart valve deployed.

The prosthetic heart valve 100 includes a valve assembly 104 preferably positioned in the annulus section 140 of the stent 102 and secured to the stent. The valve assembly 104 includes a cuff 176 and a plurality of leaflets 178 which collectively function as a one-way valve by coapting with one another. As a prosthetic aortic valve, the prosthetic heart valve 100 has three leaflets 178. However, it will be appreciated that other prosthetic heart valves with which the sealing portions of the present disclosure may be used may have a greater or lesser number of leaflets 178.

Although the cuff 176 is shown in FIG. 1 as being disposed on the luminal or inner surface of the annulus section 140, it is contemplated that the cuff 176 may be disposed on the abluminal or outer surface of the annulus section 140 or may cover all or part of either or both of the luminal and abluminal surfaces. Both the cuff 176 and the leaflets 178 may be wholly or partly formed of any suitable biological material or polymer such as, for example, polytetrafluoroethylene (PTFE), polyvinyl alcohol (PVA), ultra-high molecular weight polyethylene (UHMWPE), silicone, urethane, and the like.

The leaflets 178 may be attached along their belly portions to the cells 162 of the stent 102, with the commissure between adjacent leaflets 178 attached to commissure features 166. As can be seen in FIG. 1, each commissure feature 166 may lie at the intersection of four cells 162, two of the cells being adjacent one another in the same annular row, and the other two cells being in different annular rows and lying in end-to-end relationship. Preferably, the commissure features 166 are positioned entirely within the annulus section 140 or at the juncture of the annulus section 140 and the transition section 141. The commissure features 166 may include one or more eyelets which facilitate the suturing of the leaflet commissure to the stent 102.

The prosthetic heart valve 100 may be used to replace a native aortic valve, a surgical heart valve, or a heart valve that has undergone a surgical procedure. The prosthetic heart valve 100 may be delivered to the desired site (e.g., near the native aortic annulus) using any suitable delivery device. During delivery, the prosthetic heart valve 100 is disposed inside the delivery device in the collapsed condition. The delivery device may be introduced into a patient using a transfemoral, transapical, transseptal, transradial, transsubclavian, transaortic or any other percutaneous approach. Once the delivery device has reached the target site, the user may deploy the prosthetic heart valve 100. Upon deployment, the prosthetic heart valve 100 expands so that the annulus section 140 is in secure engagement within the native aortic annulus. When the prosthetic heart valve 100 is properly positioned inside the heart, it works as a one-way valve, allowing blood to flow from the left ventricle of the heart to the aorta, and preventing blood from flowing in the opposite direction.

Problems may be encountered when implanting the prosthetic heart valve 100. For example, in certain procedures, collapsible valves may be implanted in a native valve annulus without first resecting the native valve leaflets. The collapsible valves may have critical clinical issues because of the nature of the stenotic leaflets that are left in place. Additionally, patients with uneven calcification, bi-cuspid aortic valve disease, and/or valve insufficiency cannot be treated well, if at all, with the current collapsible valve designs.

The reliance on unevenly-calcified leaflets for proper valve placement and seating could lead to several problems, such as perivalvular leakage ("PV leak"), which can have severe adverse clinical outcomes. To reduce these adverse events, the optimal valve would anchor adequately and seal without the need for excessive radial force that could harm nearby anatomy and physiology.

PV leak may also be caused by the implantation of a valve having an expanded diameter that is too small relative to the native aortic annulus diameter, a prosthetic valve that is deployed in a tilted orientation relative to the native aortic annulus (such that the longitudinal axis of the valve and the native aortic annulus are misaligned), lack of full radial expansion of the valve due to the stent catching on calcific nodules in the native aortic annulus, and placing the valve at a non-optimal longitudinal position relative to the native aortic annulus (either too high or too low along a longitudinal axis of the native aortic annulus).

FIG. 2A is a highly schematic cross-sectional illustration of the prosthetic heart valve 100 disposed within a native valve annulus 250A. As seen in the figure, the valve assembly 104 has a substantially circular cross-section which is disposed within the non-circular native valve annulus 250A. At certain locations around the perimeter of the heart valve 100, gaps 200A form between the heart valve 100 and the native valve annulus 250A. Blood flowing through these gaps and past the valve assembly 104 of the prosthetic heart valve 100 can cause regurgitation and other inefficiencies which reduce cardiac performance. Such improper fitment may be due to suboptimal native valve annulus geometry due, for example, to calcification of the native valve annulus 250A or to unresected native leaflets.

FIG. 2B is a similar cross-sectional illustration of a prosthetic mitral valve 100B disposed within a native valve annulus 250B. As seen in the figure, the valve assembly 104B has a substantially D-shaped cross-section that is disposed within the irregularly-shaped annulus 250B. At certain locations around the perimeter of the heart valve 100B, gaps 200B form between the heart valve 100B and the native valve annulus 250B. Regurgitation and other inefficiencies may thus result after deployment of a prosthetic mitral valve. Though the following examples show aortic valves, it will be understood that the present devices and methods may be equally applicable to mitral heart valves.

FIGS. 3A-3C illustrate a prosthetic heart valve 300 in accordance with another embodiment. As can be seen in FIG. 3A, the prosthetic heart valve 300 extends between a proximal end 302 and a distal end 304, and may generally include a stent 306 formed of a plurality of struts 307, and a valve assembly 308 having a plurality of leaflets 310 and a cuff 312. The cuff 312 may include a surplus portion 322 that extends proximally of the proximal end 302 of the stent 306. In some examples, the surplus portion 322 in its straight condition may extend between about 10 mm and about 20 mm proximally of the proximal end 302 of the stent 306. The surplus portion 322 may be formed of the same material as the rest of the cuff 312 and may be formed integrally therewith from a single piece of material. Alternatively, the surplus portion 322 may be formed of the same material or a different material than the cuff 312 that is sutured, glued or otherwise affixed to the proximal end of the cuff.

FIG. 3B illustrates the prosthetic heart valve 300 after the surplus portion 322 has been rolled to form a sealing ring 350A. After assembly of the cuff 312 to the stent 306, the surplus portion 322 may be rolled outwardly in the direction of the distal end 304 to form the sealing ring 350A such that a proximal surface 323 of the sealing ring is substantially aligned in the flow direction of the stent with the proximal-most junctions 309A (FIG. 3A) of the stent. In this example, the surplus portion 322 is rolled into a generally toroidal-shaped sealing ring 350A near the proximal end 302 of the prosthetic heart valve 300 (e.g., at a position that will lie at least partially below the native valve annulus when the prosthetic heart valve is deployed into a patient). The sealing ring 350A may be formed of one complete revolution of the surplus portion 322, or of a series of revolutions (e.g., two, three or more revolutions of the surplus portion 322).

Although the sealing ring 350A is shown in FIG. 3A as having a circular cross-section, that need not be the case. The sealing ring 350A may be flattened in the flow direction, or it may have a cross-section that is square, rectangular, triangular, or other shapes. It is to be understood that all of the "sealing rings" described herein are not to be understood to be limited to having a circular cross-section. Any of the sealing rings described herein may be flattened in the flow direction, or they may have a cross-section that is square, rectangular, triangular, or other shapes.

The sealing ring 350A may maintain its shape through a variety of methods, such as by being tied to select struts 307 of the stent 306. In one example, as seen in the enlarged schematic view of FIG. 3B, end struts 360a and 360b of the stent 306 meet to form a horseshoe-shaped end 370 having a partial slot 372 therebetween. A number of locking stitches LS1 may be tied around the horseshoe-shaped ends 370, and specifically through each slot 372 and around the sealing ring 350A to keep the sealing ring from unfurling. The locking stitches LS1 may be formed of a suture, string, or any other suitable biocompatible thread.

It will be understood that, though three locking stitches are shown around the circumference of the prosthetic heart valve to couple the sealing ring 350A to the stent 306, any number of locking stitches may be used. Although the locking stitches LS1 are shown in FIGS. 3A and 3B as extending completely around the sealing ring 350A, that need not be the case. In other examples, the sealing ring 350A may be attached to the stent 306 by sutures stitched through a portion of an inner diameter of the sealing ring.

Other techniques for maintaining the shape of the sealing ring 350A may also be used including adhesive, glue, shape memory fabric, or the like. The sealing ring 350A may have a radius larger than that of the valve assembly 308, the larger radius of the sealing ring being capable of filling and/or blocking blood flow through gaps between the prosthetic heart valve 300 and the native valve annulus (not shown).

FIG. 3C illustrates the prosthetic heart valve 300 in native valve annulus 380 after formation of the sealing ring 350A as seen from the proximal end 302 (e.g., as seen from the annulus end toward the aortic end of the heart valve). The sealing ring 350A has been secured to the stent 306 via a series of locking stitches LS1. The outer diameter of the stent 306 at the proximal end is indicated with a dashed line. The sealing ring 350A extends radially outward from the outer diameter of the stent 306 at the proximal end of the prosthetic heart valve 300 by a radial distance r1. In at least some examples, the radial distance r1 may be between about 1.0 mm and about 2.5 mm. The radial distance r1 may preferably be between at least 2.0 mm.

As can be seen in FIGS. 3B and 3C, the sealing ring 350A is configured to radially expand to a diameter greater than the diameter of the proximal end 302 of the stent 306 when the stent is radially expanded, extending radially outward from the outer diameter of the stent by the radial distance r1, for example. To ensure that the sealing ring 350A radially expands to a diameter greater than the diameter of the proximal end 302 of the stent 306 when the prosthetic heart valve 300 is deployed into a patient, the sealing ring 350A, and all of the other sealing rings described herein, may have sufficient elasticity that it has a spring bias that tends to provide a force in a radially outward direction when the sealing ring is radially compressed.

However, the outward spring bias of the sealing ring 350A, and of all of the other sealing rings described herein, is preferably small enough that the sealing ring may expand a greater radial distance at locations along the circumference of the sealing ring at which there is minimal radial force applied to the sealing ring from the native anatomy (i.e., at locations at which voids or gaps between the stent 306 and the native anatomy are present), while the sealing ring may expand a lesser radial distance at locations along the circumference of the sealing ring at which there is greater radial force applied to the sealing ring from the native anatomy (i.e., locations at which there are no such voids or gaps).

FIG. 3D illustrates a heart valve 300D, which is a variant of the heart valve 300 of FIGS. 3A-3C. The heart valve 300D has a sealing ring 350D disposed at a higher location along the stent 306 than the sealing ring 350A of FIG. 3B, which may permit the prosthetic heart valve 300D to achieve improved sealing against the native annulus and the native leaflets in some patients.

Compared to the sealing ring 350A of FIGS. 3A-3C, all of the other sealing rings described herein, including the sealing ring 350D, have structures that may provide different surface areas and thicknesses of material at different longitudinal and circumferential locations relative to the stent to provide different advantages in sealing voids or gaps between the stent and the native anatomy when the heart valves are deployed into a patient. Such differences in surface areas and thicknesses of material at certain longitudinal and circumferential locations may make some sealing ring configurations preferable for certain native anatomies and other sealing ring configurations preferable for other native anatomies, depending on the anticipated locations of voids or gaps between a deployed prosthetic heart valve and the native anatomy. Such anticipated locations of voids or gaps between a deployed prosthetic heart valve and the native anatomy may be determined by a variety of methods, including imaging of the native anatomy before deployment of a prosthetic heart valve, for example.

The heart valve 300D extends between a proximal end 302 and a distal end 304, and may generally include a stent 306 formed of struts 307, and a valve assembly 308 having a plurality of leaflets 310 and a cuff 312. A surplus portion 322D of the cuff 312 has been rolled to extend around the proximal end 302 of the stent 306 to form a sealing ring 350D in a manner similar to that described above, except that the sealing ring 350D has been rolled so that the proximal surface 323D of the sealing ring lies above the proximal end 302 of the stent 306 and closer to the leaflets 310 than the sealing ring 350A (e.g., at a position that will lie within the native valve annulus when the prosthetic heart valve is deployed into a patient). After rolling the surplus portion 322D and forming the sealing ring 350D at the appropriate position, locking stitches LS2 may be coupled to the sealing ring 350D and upper junctions 309B of the proximalmost struts 307 of the stent 306 to secure the sealing ring in place.

Figure 4B:
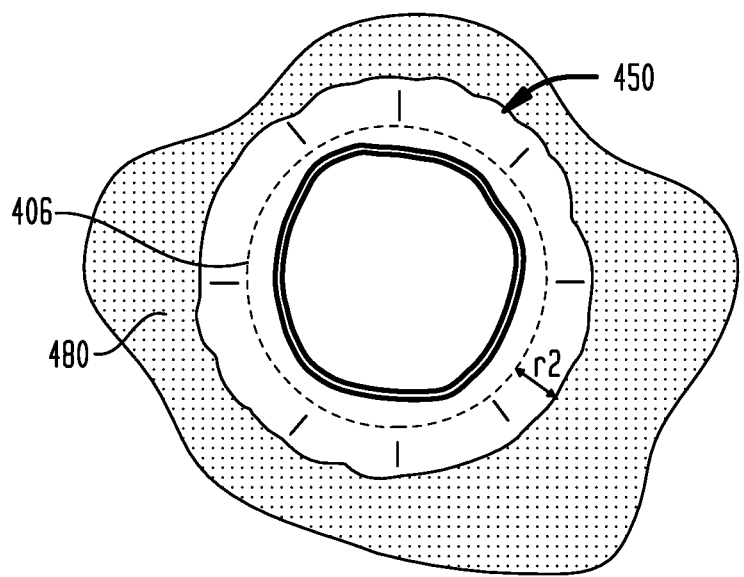
FIG. 4B is a schematic end view of the prosthetic heart valve of FIG. 4A after formation of the undulating sealing ring as seen from the annulus end toward the aortic end of the heart valve.

FIGS. 4A-4B illustrate a prosthetic heart valve 400 in accordance with another embodiment. The heart valve 400 extends between a proximal end 402 and a distal end 404, and may generally include a stent 406 formed of struts 407, and a valve assembly 408 having a plurality of leaflets 410 and a cuff 412. The cuff 412 may include a surplus portion 422 that extends proximally of the proximal end 402 of the stent 406 before rolling as described above with reference to FIG. 3B. In some examples, the surplus portion 422 in its straight condition may extend between about 5 mm and about 20 mm proximally of the proximal end 402 of the stent 406. The surplus portion 422 may be formed of the same material as the rest of the cuff 412 and may be integrally formed therewith from a single piece of material.

In this example, the surplus portion 422 is formed of a thickened material that is configured to circumferentially fold in an accordion-like fashion at certain locations to form an undulating sealing ring 450 when the prosthetic heart valve 400 is released from a delivery device. The undulating sealing ring 450 may include thin porcine pericardial tissue between about 0.005 inches and about 0.007 inches in thickness, or UHMWPE or PET fabric between about 0.003 inches and about 0.005 inches in thickness, and alternates between a series of peaks 460 and valleys 470. Compared to the sealing rings 350A and 350D described above, the undulating sealing ring 450 distributes tissue over a greater distance in the flow direction of the stent 406, thereby allowing for filling in and around voids over a greater longitudinal distance when the prosthetic heart valve 400 is deployed into a patient. Furthermore, because the undulating sealing ring 450 is configured to circumferentially fold, the sealing ring 450 may be more easily folded in an organized manner for loading into a delivery device.

Terminal sutures TS1 may attach portions of the surplus portion 422 to selected struts 407 to aid in the formation of the undulating ring 450. In some examples, the sutures TS1 may be the same sutures that are used to attach the cuff 412 to the struts 407 so that no extra steps or bulk is added. In its rolled condition, the undulating ring 450 may be annularly disposed around the stent 406 so that the valleys 470 of the sealing ring are substantially aligned in the flow direction with the proximal end 402 of the stent. As shown in FIG. 4A, the undulating ring 450 may be attached to the cuff 412 and/or the stent 406 without following the contour of the struts 407. However, in a preferred embodiment, the undulating ring 450 may be attached to the cuff 412 and/or the stent 406 following the contour of the struts 407 (FIG. 4C).

FIG. 4B illustrates the prosthetic heart valve 400 in a native valve annulus 480 after formation of the undulating sealing ring 450, as seen from the proximal end 402 (e.g., as seen from the annulus end toward the aortic end of the prosthetic heart valve). The outer diameter of the stent 406 at the proximal end is indicated with a dashed line. The undulating ring 450 extends radially outward from the outer diameter of the stent 406 at the proximal end of heart valve 400 by a radial distance r2. In at least some examples, the radial distance r2 may be between about 1.0 mm and about 10.0 mm, or between about 1.0 mm and about 2.5 mm.

FIG. 4C illustrates a heart valve 400C, which is a variant of the heart valve 400 of FIGS. 4A-4B. The heart valve 400C extends between a proximal end 402 and a distal end 404, and may generally include a stent 406 formed of struts 407, and a valve assembly 408 having a plurality of leaflets 410 and a cuff 412.

A sealing ring 450C may be annularly disposed around the abluminal surface of the stent 406 at the proximal end 402 of the prosthetic heart valve 400. The sealing ring 450C may alternate between a series of peaks 460C and valleys 470C and may radially expand to a diameter greater than the diameter of the proximal end of the stent 406, as described above with reference to the sealing ring 350A of FIGS. 3A-3C.

Similar to the sealing ring 450 shown in FIGS. 4A-4B, the sealing ring 450C may be formed of a thickened material that is configured to circumferentially fold in an accordion-like fashion at certain locations to form an undulating sealing ring when the prosthetic heart valve 400C is released from a delivery device.

As shown in FIG. 4C, the valleys 470C of the sealing ring 450C may be stitched to the proximalmost junctions 409A of the stent 406, and the peaks 460C of the sealing ring may be stitched to upper junctions 409B of the proximalmost struts 407 of the stent. As shown in FIG. 4C, in a preferred embodiment, the undulating ring 450C may be attached to the cuff 412 and/or the stent 406 following the contour of the struts 407. Such an attachment of the undulating ring 450C following the contour of the struts 407 may permit a reduction in the number of sutures needed to attach the sealing ring to the cuff 412 and/or the stent 406, which may help to reduce the crimped diameter of the prosthetic valve 400C.

The sealing ring 450C may be formed, for example, from a long, thin rectangle of material about 10 mm in width that is folded approximately in half longitudinally, and the opposed longitudinal edges may be stitched to one another to create a flattened tube about 5 mm in diameter. The lateral ends of the flattened tube may be stitched to one another to create the sealing ring 450C.

The longitudinal seam of the sealing ring 450C may be stitched to an abluminal surface of the cuff 412 and select struts 407 of the stent 406 by sutures that secure the sealing ring in place. In some examples, the sutures are the same sutures as are used to attach the cuff 412 to the struts 407 so that no extra steps or bulk is added. Alternatively, the sealing ring 450C may be formed from a surplus portion of the cuff 412 that is rolled to form a sealing ring in a manner similar to that described above. Any of the sealing rings disclosed herein may be formed using any one of the aforementioned formation methods.

In one example, the sealing ring 450C may be made of a thin tubular fabric material. In other examples, the sealing ring 450C may include thin porcine pericardial tissue between about 0.005 inches and about 0.007 inches in thickness, or UHMWPE or PET fabric between about 0.003 inches and about 0.005 inches in thickness. Alternatively, a variety of other materials may be used, including bovine tissue (e.g., glycerol impregnated or freeze dried), tissue with support structures therein, wire mesh, radiopaque wire, fabric, braided or woven fabric (e.g., PTFE, PTE, or UHMWPE), fabric coated with PTFE or collagen, or a multi-layered composite of one or more of the aforementioned materials (e.g., a fabric and tissue composite). Any of the sealing rings disclosed herein may be made of any one of the aforementioned materials or a combination thereof.

The sealing ring 450C may be at least partially radiopaque, i.e., the sealing ring may include one or more materials having enhanced visibility to a user under fluoroscopy. For example, the sealing ring 450C may be include fabric or wire mesh material having radiopaque fibers or entirely comprised of radiopaque fibers. The sealing ring 450C may include radiopaque marker beads, a thin radiopaque wire, radiopaque paint, or impregnation by soaking in a radiopaque material such as silver, iodine, barium, platinum, or the like. Any of the sealing rings disclosed herein may be made of any one of the aforementioned radiopaque materials or a combination thereof.

FIG. 4D illustrates a prosthetic heart valve 400D, which is a variant of the prosthetic heart valve 400C of FIG. 4C. The prosthetic heart valve 400D may be identical to the prosthetic heart valve 400C, except for the sealing ring 450D, in which the valleys 470D are stitched to the proximalmost junctions 409A of the stent 406, but the peaks 460D may be located about half-way between the proximalmost junctions and upper junctions 409B.

The peaks 460D of the sealing ring 450D may be stitched to the abluminal surface of the cuff 412, or alternatively, the portions of the sealing ring containing the peaks may not be stitched to the cuff or the struts 407. In embodiments in which the portions of the sealing ring 450D containing the peaks are not stitched to the cuff 412 or the struts 407, the unstitched portions of the sealing ring may be able to move relative to the cuff and struts during sheathing or resheathing of the prosthetic heart valve 400D, thereby reducing the tissue bulk at any particular longitudinal location along the stent 406, which may help reduce the profile (i.e., diameter) of the prosthetic heart valve when it is in a radially-compressed condition in the delivery device.

FIGS. 5A-5E illustrate variants of sealing rings that may be used with prosthetic heart valves 400, 400C, or 400D in place of the sealing rings shown in FIGS. 4A-4D. Each of the sealing rings 550A-550E shown in FIGS. 5A-5E may be formed in the same manner, attached to the stent and cuff in the same manner, and made of the same material or materials described above with reference to the sealing rings 450, 450C, and 450D. Each of the sealing rings 550A-550E may be attached to a stent in any location along the longitudinal axis of the stent. A prosthetic heart valve, such as the prosthetic heart valve 400C, may include one of the sealing rings 550A-550E, or alternatively, the prosthetic heart valve may include two or more of the sealing rings, as will be described in more detail below.

FIG. 5A shows a sealing ring 550A in the shape of a toroid similar to the toroidal-shaped sealing ring 350A shown in FIGS. 3B and 3C. FIG. 5B shows a sealing ring 550B in the shape of a bent or saddle-shaped toroid that alternates between peaks 560B and valleys 570B around the circumference of the sealing ring, the peaks and valleys being substantially evenly distributed about the circumference. As shown in FIG. 5B, the sealing ring 550B has two peaks 560B and two valleys 570B, but the sealing ring may have other numbers of peaks and valleys, such as three, for example.

FIG. 5C shows a sealing ring 550C having a zigzag shape, similar to the zigzag shape shown in FIG. 4C. The sealing ring 550C alternates between peaks 560C and valleys 570C around the circumference of the sealing ring, the peaks and valleys being substantially evenly distributed about the circumference. As shown in FIG. 5C, the sealing ring 550C has nine peaks 560C and nine valleys 570C, but the sealing ring may have other numbers of peaks and valleys, such as three or six, for example. As shown in FIG. 4C, a sealing ring having a zigzag shape may be stitched to the stent and the cuff along the struts. However, in other embodiments, the sealing ring 550C may be stitched to the stent and/or the cuff at other locations.

FIG. 5D shows a sealing ring 550D having a zigzag shape with alternating peak heights. The sealing ring 550D alternates between peaks 560D and valleys 570D around the circumference of the sealing ring, the peaks and valleys being substantially evenly distributed about the circumference. As shown in FIG. 5D, the sealing ring 550D has eight peaks 560D and eight valleys 570D, but the sealing ring may have other numbers of peaks and valleys, such as four or six, for example.

The peaks 560D include low peaks 561 that extend by a first height H1 above the valleys 570D and high peaks 562 that extend by a second height H2 above the valleys, the second height being greater than the first height. As shown in FIG. 5D, the peaks 560D may include four low peaks 561 and four high peaks 562, with one low peak separating adjacent ones of the high peaks. In other embodiments, there may be other numbers of high and low peaks. For example, a sealing ring having varying peak heights may include six low peaks and three high peaks, with two low peaks separating adjacent ones of the high peaks. In another example, a sealing ring having varying peak heights may include three low peaks and six high peaks, with two high peaks separating adjacent ones of the low peaks.

FIG. 5E shows a stacked arrangement of two sealing rings 550D each having a zigzag shape with alternating peak heights. As shown in FIG. 5E, the two sealing rings 550D are identical in structure and are aligned with one another such that the peaks 560D and valleys 570D of the upper sealing ring are substantially aligned longitudinally with the peaks and valleys of the lower sealing ring, and such that the low peaks 561 and high peaks 562 of the upper sealing ring are substantially aligned longitudinally with the low peaks and high peaks of the lower sealing ring. In other embodiments, the peaks 560D and valleys 570D of the two sealing rings 550D, and the low peaks 561 and the high peaks 562 of the two sealing rings need not be longitudinally aligned. In other embodiments, the two sealing rings need not have an identical structure.

FIG. 5F shows a sealing ring 550F having a toroidal shape, similar to the toroidal-shaped sealing ring 550A shown in FIG. 5A. The sealing ring 550F has openings 563 in a top surface 564 thereof. The openings 563 may be round holes or may be holes having any other shape or slits having any shape. The sealing ring 550F may be attached to a stent and cuff of a prosthetic heart valve in a similar manner as that described above with reference to the sealing ring 450C shown in FIG. 4C.

When the sealing ring 550F is attached to a stent and cuff of a prosthetic heart valve, the openings 563 and the top surface 564 will preferably face toward the distal end of the stent. When deployed in a patient, the openings 563 may allow the sealing ring 550F to fill with blood, which may augment the sealing ability of the sealing ring against the native aortic annulus or other native tissue structures. Instead of or in addition to the openings 563, the sealing ring 550F may include expanding materials within the interior of the sealing ring, such as polyacrylimide or other hydroscopic materials, PVA, shape memory foam, bovine gelatin or collagen, or the like.

In another variation shown in FIGS. 6A-6B, a prosthetic heart valve 600 extends between a proximal end 602 and a distal end 604, and may generally include a stent 606 formed of struts 607, and a valve assembly 608 having a plurality of leaflets 610 and a cuff 612. The cuff 612 may include an extended surplus portion 622 that extends proximally of the proximal end 602 of the stent 606. In some examples, the surplus portion 622 may extend in its straight condition between about 5.0 mm and about 10.0 mm proximally of the proximal end 602 of the stent 606. The surplus portion 622 may be formed of the same material as the rest of the cuff 612 and may be formed integrally therewith from a single piece of material.

In this example, the surplus portion 622 deploys into a substantially flat sealing ring 650, which extends radially outward to a diameter greater than the diameter of the proximal end of the stent 606. FIG. 6B illustrates the prosthetic heart valve 600 in a native valve annulus 680 after formation of the sealing ring 650, as seen from the proximal end 602 (e.g., as seen from the annulus end toward the aortic end of the heart valve. The outer diameter of the stent 606 at the proximal end is indicated with a dashed line. The sealing ring 650 extends radially outward from the outer diameter of the stent 606 at the proximal end of the prosthetic heart valve 600 by a radial distance r3. In at least some examples, the radial distance r3 is between about 2 mm and about 10 mm. In this embodiment, the sealing ring 650 does not fill the gaps between the prosthetic heart valve 600 and the native annulus 650, but rather extends over the gaps to occlude blood flow through them.

In a variation of the sealing ring 650, FIGS. 6C-6D show a sealing ring 650C that may be made from a material separate from the cuff 612, such as a thin flat skirt cut from a strip or circle of porcine tissue without a seam. In one example, the circle of tissue comprising the sealing ring 650C may have an inner diameter D1 of about 29 mm, an outer diameter D2 of about 34 mm, and a width W1 between the inner diameter and an outer diameter of about 5 mm. As shown in FIG. 6D, an inner edge 651 of the sealing ring 650C may be sutured to the stent 606 and the cuff 612 near the proximal end 602, using a running stitch, for example. An outer edge 652 of the sealing ring 650C may be a free edge that is not sutured to the stent 606 or the cuff 612, and the outer edge may undulate naturally as shown in FIG. 6D. In this example, the outer edge 652 of the sealing ring 650C may extend up to 5 mm radially outward from the stent 606.

FIG. 7 illustrates a prosthetic heart valve 700, which is a variant of the prosthetic heart valve 100 of FIG. 1. The heart valve 700 extends between a proximal end 702 and a distal end 704, and may generally include a stent 706 formed of struts 707, and a valve assembly 708 having a plurality of leaflets 710 and a cuff 712.

As shown in FIG. 7, in the prosthetic heart valve 700, the cuff 712 may extend over a greater distance in a flow direction of the stent 706 compared to the cuff 112 of FIG. 1. For example, when the stent 706 is in an expanded use condition, a landing zone (i.e., continuous cylindrical portion) of the cuff 712 may extend over a length of about 16 mm to about 18 mm in the flow direction from the proximal end 702 toward the distal end 704, compared to a landing zone of about 8 mm to about 10 mm for the cuff 112 of the prosthetic heart valve 100. Furthermore, the bellies of the leaflets 710 may be attached to the stent 706 and the cuff 712 a greater distance away from the proximal end 702 in the flow direction than the bellies of the leaflets 110 of the prosthetic heart valve 100. In one example, the belly of each of the leaflets 710 may be attached to the stent 706 and the cuff 712 a distance D3 of at least 10 mm from the proximal end 702 of the stent.

The prosthetic valve 700 having a cuff 712 having a relatively large landing zone may be used with any of the sealing rings disclosed herein. The large landing zone of the cuff 712 may permit a plurality of sealing rings to be attached thereto, the sealing rings separated from one another in the flow direction (e.g., FIG. 14B).

FIGS. 8A-8E illustrate prosthetic heart valve configurations that have sealing rings that are variants of the sealing ring 450C shown in FIG. 4C, in which the sealing ring embodiments are attached to the stent and cuff below (i.e., closer to the proximal end of the stent) the locations at which the bellies of the leaflets are attached to the stent and cuff. In each of these embodiments, as well as the embodiments described below, the sealing ring has a generally tubular configuration which, in its expanded condition, projects radially outward from the annulus section of the prosthetic heart valve.

FIGS. 8A-8B illustrate a heart valve 800 that extends between a proximal end 802 and a distal end 804, and that may generally include a stent 806 formed of struts 807, and a valve assembly 808 having a plurality of leaflets 810 and a cuff 812. The sealing ring 850 may have a shape that is similar to the bent or saddle-shaped toroid of the sealing ring 550B shown in FIG. 5B.

The sealing ring 850 alternates between peaks 860 and valleys 870 around the circumference of the sealing ring, the peaks and valleys being substantially evenly distributed about the circumference. The sealing ring 850 has three peaks 860 and three valleys 870 positioned between adjacent ones of the peaks. The peaks 860 are substantially aligned in the flow direction with the commissure features 866, and the valleys 870 are substantially aligned in the flow direction with the lowest portion 811 of the attachment of the bellies of the leaflets 810 to the stent 806 and the cuff 812.

The entirety of the sealing ring 850 is attached to the stent 806 and cuff 812 below the positions at which the bellies of the leaflets 810 are attached to the stent and cuff. Such a configuration may more evenly distribute the material of the leaflets and the sealing ring along the length of the prosthetic heart valve 800, which may permit a smaller crimped diameter of the prosthetic heart valve when loaded into a delivery device.

In one example, a single suture may be stitched around the entire circumference of the stent 806 to attach the sealing ring 850 to the stent and the cuff 812. The sealing ring 850 may be stitched to the struts 807 at each location at which the sealing ring crosses a strut, and the sealing ring may be stitched to the tissue of the cuff 812 at locations between the struts. As described above with reference to FIGS. 4A and 4B, the sutures used to attach the sealing ring 850 to the struts 807 (and any of the other sealing rings described herein) may be the same sutures that are used to attach the cuff 812 to the struts so that no extra steps or bulk is added.

As can be seen in FIG. 8A, the valleys 870 of the sealing ring 850 may be attached to the proximalmost junctions 809A of the stent 806, and the peaks 860 of the sealing ring may be attached to upper junctions 809B of the proximalmost struts 807 of the stent.

FIG. 8C shows a sealing ring 850C that is a variant of the sealing ring 850 of FIGS. 8A-8B. The sealing ring 850C may have a shape that is similar to the bent or saddle-shaped toroid of the sealing ring 850 with three peaks and three valleys, but the peaks 860C of the sealing ring 850C are attached to the stent 806 and/or the cuff 812 above the upper junctions 809B of the proximalmost struts of the stent. Thus, in this embodiment, the entire sealing ring 850C does not lie below the positions at which the bellies of the leaflets 810 are attached to the stent 806 and the cuff 812, but rather there is some overlap between the sealing ring and the leaflets. While this embodiment provides a greater sealing area between the prosthetic heart valve and the surrounding tissue, the crimped profile of the prosthetic valve is not as small as that achievable with the sealing ring 850.

FIG. 8D shows the sealing ring 850 of FIGS. 8A-8B in another location relative to the leaflets 810. In this variation, the valleys 870 of the sealing ring 850 are substantially aligned in the flow direction with the commissure features 866, and the peaks 860 are substantially aligned in the flow direction with the lowest attached portions 811 of the bellies of the leaflets 810. As with the embodiment of FIGS. 8A-8B, the entirety of the sealing ring 850 lies below the positions at which the bellies of the leaflets 810 are attached to the stent 806 and the cuff 812, enabling a smaller crimp profile to be achieved.

FIG. 8E shows a sealing ring 850E that is another variant of the sealing ring 850 of FIGS. 8A-8B. The sealing ring 850E has five peaks 860E and five valleys 870E forming a zigzag shape somewhat similar to that of the sealing ring 550C of FIG. 5C, but alternating legs of the zigzag configuration have different lengths. That is, legs 863 have a longer length than legs 864. This enables the legs 864 to directly overlie and be attached to certain struts 807 of the stent 806, while the legs 863 may not be attached to the stent 806 or the cuff 812. Such method of attachment provides for easier expanding and collapsing of the prosthetic heart valve. One of the peaks 860E is substantially aligned in the flow direction with a commissure feature 866, while others of the peaks are close to being aligned in the flow direction with the lowest attached portions 811 of the bellies of the leaflets 810. Some of the valleys 870E are substantially aligned in the flow direction with the lowest attached portions 811 of the bellies of the leaflets 810, while others of the valleys are close to being aligned in the flow direction with the commissure features 866.

FIGS. 9A-9C illustrate prosthetic heart valve configurations that have embodiments of sealing rings that are variants of the sealing ring 450C shown in FIG. 4C, in which the sealing ring embodiments are attached to the stent and cuff both above and below the locations at which the bellies of the leaflets are attached to the stent and cuff. In these embodiments, the material of the sealing ring may be more evenly distributed along the length of the prosthetic heart valve than an embodiment where the sealing ring is distributed along a very small portion of the length of the prosthetic heart valve (e.g., the sealing ring 550A), which may permit a smaller crimped diameter of the prosthetic heart valve when loaded into a delivery device.

FIGS. 9A-9B illustrate a heart valve 900 that extends between a proximal end 902 and a distal end 904, and that may generally include a stent 906 formed of struts 907, and a valve assembly 908 having a plurality of leaflets 910 and a cuff 912. The sealing ring 950 may have a shape with alternating height zigzag features similar to those of the sealing ring 550D shown in FIG. 5D, but the sealing ring 950 has six peaks 960 and six valleys 970, including three low peaks 961 that extend to a first height H1 above the valleys and three high peaks 962 that extend to a second height H2 above the valleys, the second height being greater than the first height.

As can be seen in FIG. 9A, each low peak 961 is disposed between adjacent ones of the high peaks 962, and each high peak is disposed between adjacent ones of the low peaks. The low peaks 961 are substantially aligned in the flow direction with the commissure features 966, while the high peaks 962 are substantially aligned in the flow direction with the lowest attached portions 911 of the bellies of the leaflets 910.

Such a configuration of a sealing ring having low peaks 961 and high peaks 962 at alternating heights may permit a smaller crimped diameter of the prosthetic heart valve when loaded into a delivery device. When the prosthetic heart valve is crimped into a delivery device, the low peaks 961 will be disposed at a different longitudinal location along the stent 906 than the high peaks 962, thereby distributing the bulk of the peaks so that only half of the peaks are at any single longitudinal location.

In one example, a single suture may be stitched around the entire circumference of the stent 906 to attach the sealing ring 950 to the stent and the cuff 912. The sealing ring 950 may be stitched to the struts 907 along the entire circumference of the sealing ring. As can be seen in FIG. 9A, the valleys 970 of the sealing ring 950 may be attached to the proximalmost junctions 909A of the stent 906, and the low peaks 961 of the sealing ring may be attached to upper junctions 909B of the proximalmost struts 907 of the stent. The high peaks 962 may be attached to upper junctions 909C of certain cells in a first full row 913 of complete cells 915 adjacent the proximal end 902 of the stent 906.

FIG. 9C shows a sealing ring 950C that is a variant of the sealing ring 950 of FIGS. 9A-9B. The sealing ring 950C has three peaks 960C and three valleys 970C. The valleys 970C of the sealing ring 950C are substantially aligned in the flow direction with the commissure features 966, while the peaks 960C are substantially aligned in the flow direction with the lowest attached portions 911 of the bellies of the leaflets 910.

FIGS. 10A-10D illustrate prosthetic heart valve configurations that have embodiments of sealing rings that are variants of the sealing ring 450C shown in FIG. 4C, in which the sealing ring embodiments are attached to the stent and cuff both above and below the locations at which the bellies of the leaflets are attached to the stent and cuff, and in which portions of the sealing ring extending substantially orthogonally to the longitudinal axis may be attached to the cuff along their length or held up under tension when the stent is expanded.

In embodiments in which portions of the sealing ring are not attached to the valve stent, the material of the sealing ring may readily move along the length of the prosthetic heart valve when the valve is loaded into a delivery device, which may permit a smaller crimped diameter of the prosthetic heart valve. For example, in embodiments such as those shown in FIGS. 10A-10D, the portions of the sealing rings that are unattached to the cuff may be pushed to a different longitudinal location along the stent than the bellies of the leaflets during crimping of the prosthetic heart valve, thereby permitting a smaller crimped diameter of the prosthetic heart valve.

Figure 10A:
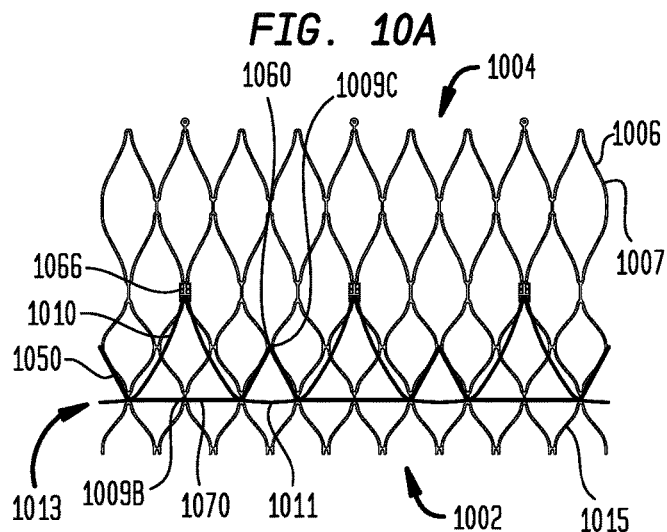
FIG. 10A is a developed view of the stent, sealing ring, and leaflets of another embodiment of a heart valve having a sealing ring intended to fill irregularities between the heart valve and the native valve annulus.
Figure 10B:
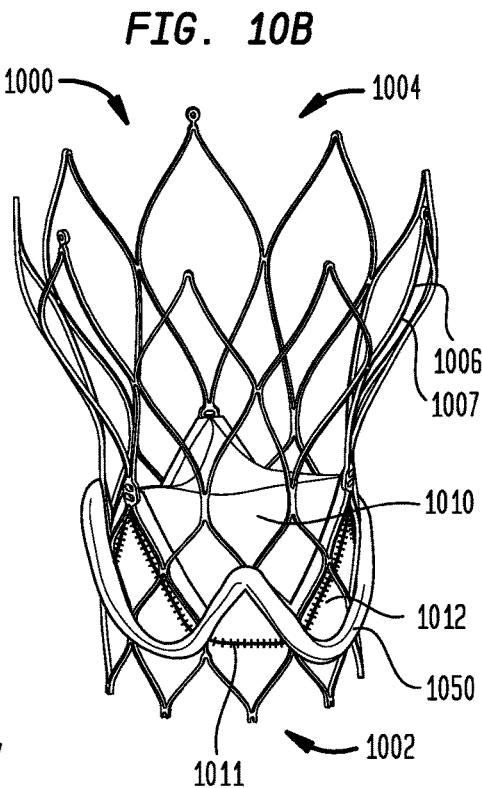
FIG. 10B is a side view of a heart valve having the stent, sealing ring, and leaflets of FIG. 10A.

FIGS. 10A-10B illustrate a heart valve 1000 that extends between a proximal end 1002 and a distal end 1004, and that may generally include a stent 1006 formed of struts 1007, and a valve assembly 1008 having a plurality of leaflets 1010 and a cuff 1012. The sealing ring 1050 may have a shape with zigzag features similar to those of the sealing ring 550C shown in FIG. 5C, but the sealing ring 1050 has three peaks 1060 and three valleys 1070, and the three valleys may include linear portions that extend substantially orthogonally to the longitudinal axis and that are either attached to the cuff 1012 along the length thereof or unattached to the cuff and stent 1006, but held up under tension when the stent is expanded.

As can be seen in FIG. 10A, the peaks 1060 are substantially aligned in the flow direction with the lowest attached portions 1011 of the bellies of the leaflets 1010, while the valleys 1070 are substantially aligned in the flow direction with the commissure features 1066. The peaks 1060 may be attached to upper junctions 1009C of certain cells in a first full row 1013 of complete cells 1015 adjacent the proximal end 1002 of the stent 1006. The valleys 1070 may be attached to upper junctions 1009B of the proximalmost struts 1007 of the stent 1006 and to the cuff 1012 between the upper junctions, or they may not be attached to either the cuff or the stent, but held up under tension when the stent is expanded. In the attached position of the sealing ring 1050, the valleys 1070 may be substantially aligned in the circumferential direction with the lowest attached portions 1011 of the bellies of the leaflets 1010.

Figure 10C:
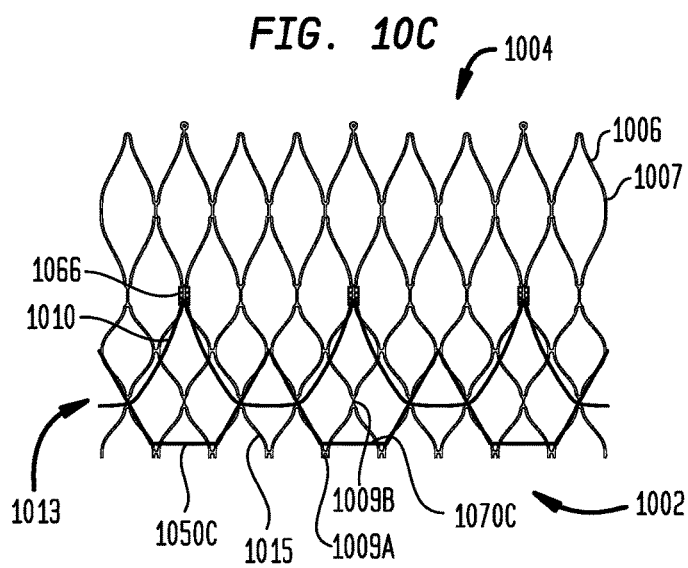
FIGS. 10C and 10D are developed views of variations of the stent, sealing ring, and leaflets of FIG. 10A.

FIG. 10C shows a sealing ring 1050C that is the same as the sealing ring 1050 of FIGS. 10A-10B, except that the valleys 1070C are located closer to the proximal end 1002 of the stent. In that regard, the valleys 1070C of the sealing ring 1050C include linear portions that extend substantially orthogonally to the longitudinal axis and that may not be attached to the cuff 1012 or the stent. These linear portions may be located about half-way between the lower junctions 1009A and the upper junctions 1009B of the proximalmost struts 1007 of the stent.

Figure 10D:
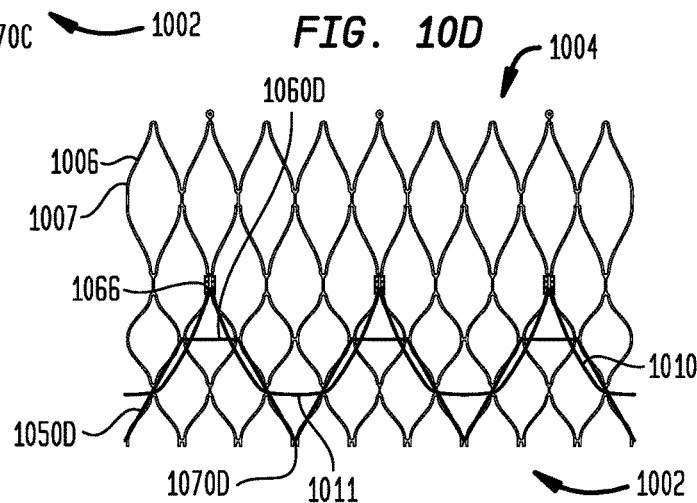

FIG. 10D shows a sealing ring 1050D that is another variant of the sealing ring 1050 of FIGS. 10A-10B. The sealing ring 1050D has three peaks 1060D and three valleys 1070D, however, the peaks include linear portions that extend substantially orthogonally to the longitudinal axis and the valleys have a substantially V-shape. The peaks 1060D are substantially aligned in the flow direction with the commissure features 1066, while the valleys 1070D are substantially aligned in the flow direction with the lowest attached portions 1011 of the bellies of the leaflets 1010. The valleys 1070D may be attached to the proximalmost 1009A of the stent. The peaks 1060D may be attached to the cuff 1012 between the upper junctions 1009C of certain cells in the first full row 1013 of complete cells 1015 adjacent the proximal end 1002 of the stent 1006, or they may not be attached to either the cuff or the stent, but held up under tension when the stent is expanded. Between the peaks 1060D and the valleys 1070D, the sealing ring 1050D may be attached directly to struts 1007 of the stent 1006.

FIGS. 11A-11H illustrate prosthetic heart valve configurations that have embodiments of sealing rings that are variants of the sealing ring 450C shown in FIG. 4C, in which the sealing ring embodiments are attached to the stent and cuff at least partially along the attachment contour of the bellies of the valve leaflets to the stent/cuff, so that the sealing ring can integrate or replace an existing underwire that may be used to reinforce the cuff where the bellies of the leaflets attach to same.

Figure 11A:
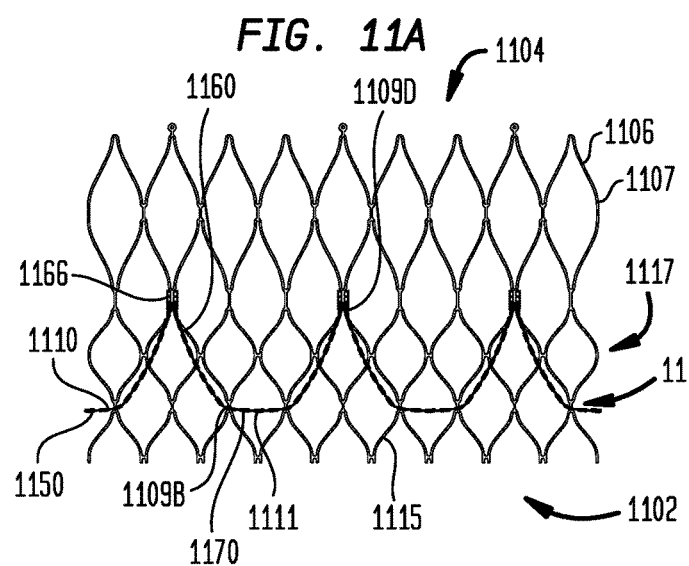
FIG. 11A is a developed view of the stent, sealing ring, and leaflets of another embodiment of a heart valve having a sealing ring intended to fill irregularities between the heart valve and the native valve annulus.
Figure 11B:
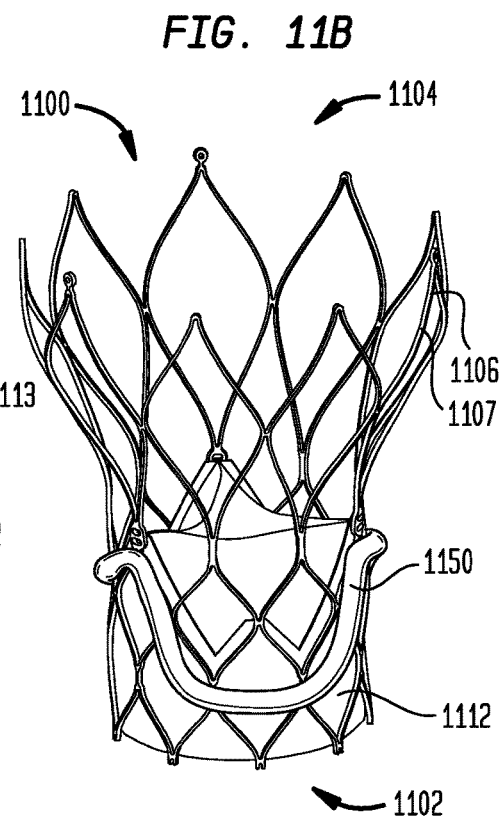
FIG. 11B is a side view of a heart valve having the stent, sealing ring, and leaflets of FIG. 11A.

FIGS. 11A-11B illustrate a heart valve 1100 that extends between a proximal end 1102 and a distal end 1104, and that may generally include a stent 1106 formed of struts 1107, and a valve assembly 1108 having a plurality of leaflets 1110 and a cuff 1112. The sealing ring 1150 has a generally scalloped shape including three sharp peaks 1160 and three smoothly-curved valleys 1170.

As can be seen in FIG. 11A, the sealing ring 1150 is attached to the stent 1106 and the cuff 1112 at the same locations that the leaflets 1110 are attached to the stent and cuff. As a result, the peaks 1160 are substantially aligned in the flow direction with the commissure features 1166, while the valleys 1170 are substantially aligned in the flow direction with the lowest attached portions 1111 of the bellies of the leaflets 1110. The peaks 1160 may be attached to the commissure features 1166 or to upper junctions 1109D of certain cells in a second full row 1117 of complete cells 1115 above the first full row 1113. The valleys 1170 may be attached to upper junctions 1109B of the proximalmost struts 1107 of the stent and to the cuff 1112 between the upper junctions.

In this embodiment, a single underwire formed of the same material as the struts 1107 may be used to provide reinforcement to both the sealing ring 1150 and the cuff 1112. In one example, an underwire may be stitched to a surface of the cuff 1112, and the stitches that attach the sealing ring 1150 to the cuff 1112 may extend around the underwire. In another example, an underwire may be disposed inside of the sealing ring 1150, and the stitches that attach the bellies of the leaflets 1110 to the cuff 1112 may extend into the sealing ring and around the underwire. Thus, in this arrangement, the leaflets, the underwire, and the sealing ring may be attached to the prosthetic valve with a single set of sutures. In a particular example in which the sealing ring 1150 is made of a fabric material, the fabric material may provide sufficient reinforcement to the cuff 1112 that an underwire may be omitted from the prosthetic heart valve 1100.

Figure 11C:
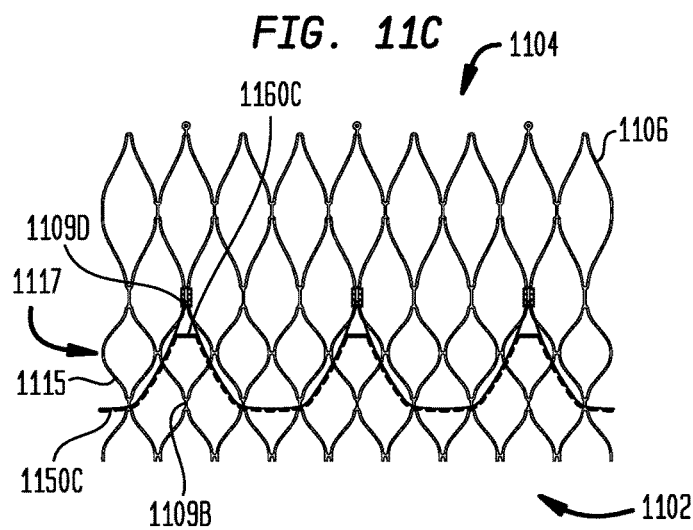
FIG. 11C is a developed view of the stent, sealing ring, and leaflets of another embodiment of a heart valve having a sealing ring intended to fill irregularities between the heart valve and the native valve annulus.
Figure 11D:
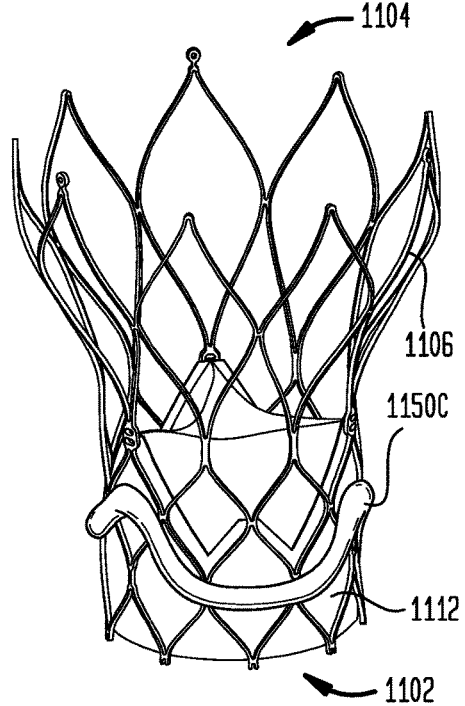
FIG. 11D is a side view of a heart valve having the stent, sealing ring, and leaflets of FIG. 11C.

FIGS. 11C-11D show a sealing ring 1150C that is the same as the sealing ring 1150 of FIGS. 11A-11B, except that the peaks 1160C are truncated so as to be located closer to the proximal end 1102 of the stent. As can be seen in FIGS. 11C-11D, the peaks 1160C may include linear portions that extend substantially orthogonally to the longitudinal axis and that may not be attached to the cuff 1112 or the stent 1106. These linear portions may be located about half-way between the upper junctions 1109B of the proximalmost struts of the stent and the upper junctions 1109D of certain cells in the second full row 1117 of complete cells.

Figure 11E:
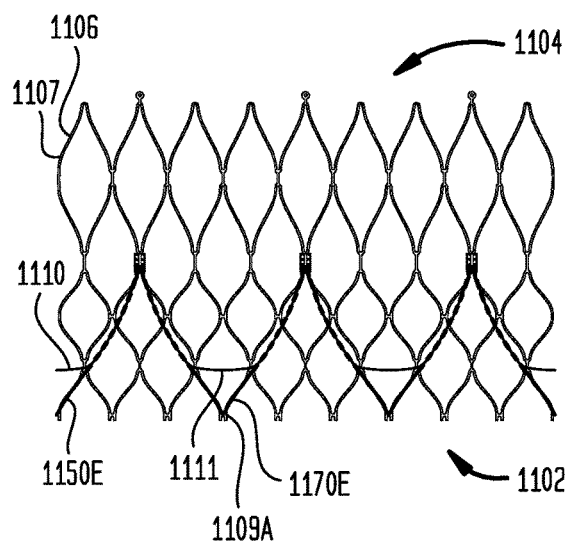
FIGS. 11E-11H are developed views of variations of the stent, sealing ring, and leaflets of FIG. 11A.

FIG. 11E shows a sealing ring 1150E that is another variant of the sealing ring 1150 of FIGS. 11A-11B. The sealing ring 1150E is the same as the sealing ring 1150 of FIGS. 11A-11B, except that the valleys 1170E extend down to the proximalmost junctions 1109A of the stent 1106, and the contour of the valleys does not follow the contour of the bellies of the leaflets 1110.

Figure 11F:
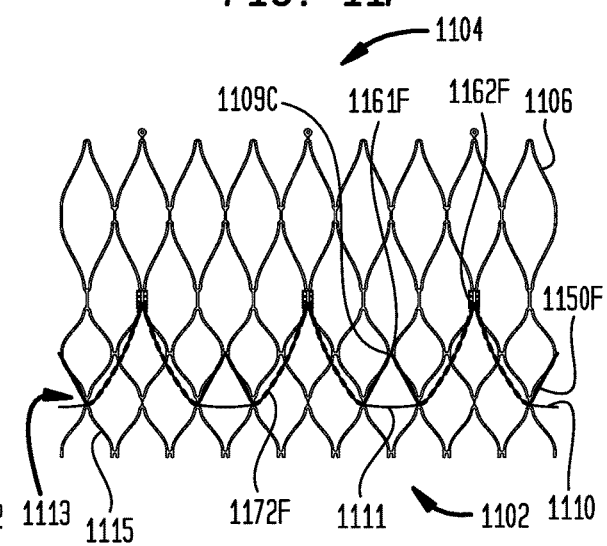

FIG. 11F shows a sealing ring 1150F that is the same as the sealing ring 1150 of FIGS. 11A-11B, with sharp peaks 1162F and smoothly curved valleys 1172F. However, in this embodiment, the valleys 1172F each include a lower peak 1161F that does not follow the contour of the bellies of the leaflets 1110. The upper peaks 1162F follow the contour of the bellies of the leaflets 1110, but the lower peaks 1161F extend above the lowest attached portions 1111 of the bellies of the leaflets, and are attached to the stent 1106 at the upper junctions 1109C of the first full row 1113 of complete cells 1115.

Figure 11G:
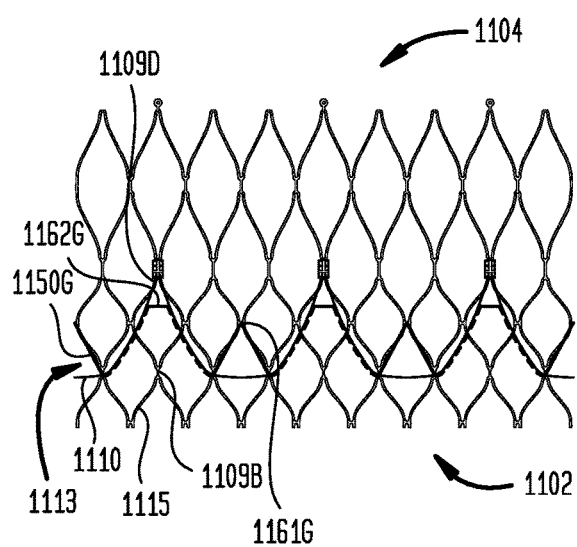

FIG. 11G shows a sealing ring 1150G that is the same as the sealing ring 1150F of FIG. 11F, except that the upper peaks 1162G are truncated. That is, the second peaks 1162G include linear portions that extend substantially orthogonally to the longitudinal axis and that are either attached to the cuff 1112 along their lengths or are not attached to the cuff or the stent 1106, but rather are held up under tension when the stent is expanded. The linear portions of the second peaks 1162G may be located about half-way between the upper junctions 1109B of the proximalmost struts of the stent and the upper junctions 1109D of certain cells in the second full row 1117 of complete cells 1115.

Figure 11H:
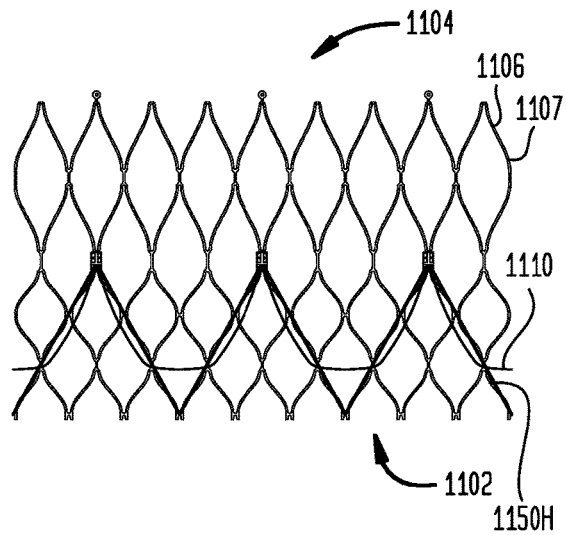

FIG. 11H shows a sealing ring 1150H that is the same as the sealing ring 1150E of FIG. 11E, except that sealing ring 1150H is attached to the stent 1106 and the cuff 1112 along the contour of certain struts 1107 of the stent, only partially following the attachment contour of the bellies of the leaflets 1110 to the stent 1106 and the cuff 1112.

FIGS. 12A-12K illustrate that have embodiments of sealing rings that are variants of the sealing ring 450C shown in FIG. 4C, in which the sealing ring embodiments have at least one vertical discontinuity, such that the sealing ring does not extend continuously around the entire circumference of the stent.

Figure 12A:
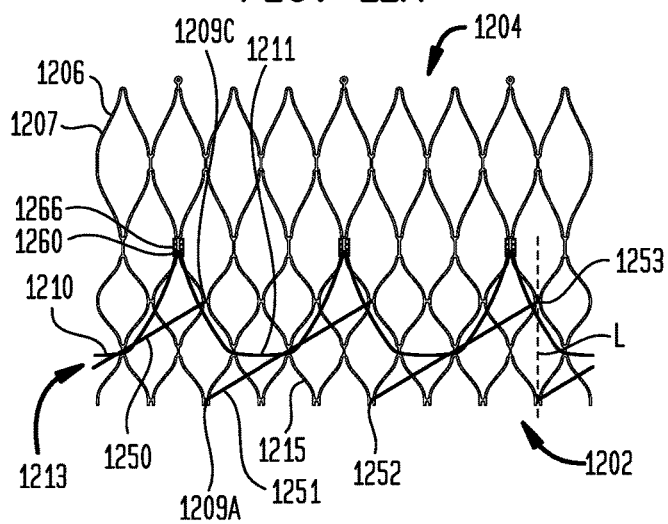
FIG. 12A is a developed view of the stent, sealing ring, and leaflets of another embodiment of a heart valve having a sealing ring intended to fill irregularities between the heart valve and the native valve annulus.
Figure 12B:
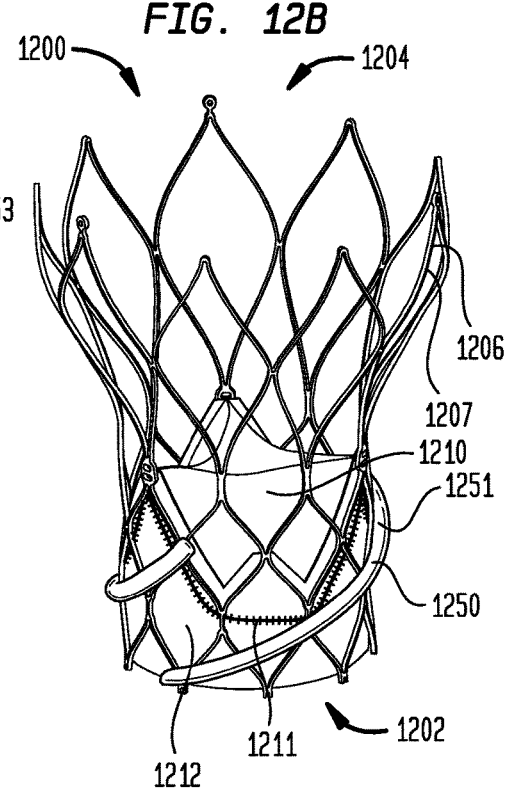
FIG. 12B is a side view of a heart valve having the stent, sealing ring, and leaflets of FIG. 12A.

FIGS. 12A-12B illustrate a heart valve 1200 that extends between a proximal end 1202 and a distal end 1204, and that may generally include a stent 1206 formed of struts 1207, and a valve assembly 1208 having a plurality of leaflets 1210 and a cuff 1212. As shown in FIG. 12A, the sealing ring 1250 may have three discontinuous sections 1251, each such section extending around about one-third of the circumference of the stent 1206. Each section 1251 may extend from a location below the lowest point at which the bellies of the leaflets 1210 are attached to the stent 1206 and cuff 1212 to a location above that lowest point.

As can be seen in FIG. 12A, each discontinuous section 1251 extends in both a circumferential direction and a flow direction of the stent 1206, from a low end 1252 adjacent the proximal end 1202 of the stent to a high end 1253 spaced apart from the distal end 1204. The low end 1252 of each section 1251 may be attached to proximalmost junctions 1209A of the stent 1206, and the high end 1253 may be attached to upper junctions 1209C of certain cells in the first full row 1213 of complete cells 1215.

The high end 1253 of each section 1251 is aligned in the flow direction with, but vertically displaced from, the low end 1252 of an adjacent discontinuous section, such that, for each discontinuous section, an imaginary line L can be drawn in the flow direction that intersects the high end of the section and the low end of the adjacent section. As shown in FIG. 12A, the imaginary line L that intersects the high end 1253 of one section 1251 and the low end 1252 of the adjacent discontinuous section is located circumferentially between a commissure feature 1266 and the lowest attached portion 1211 of a corresponding one of the bellies of the leaflets 1210.

Figure 12C:
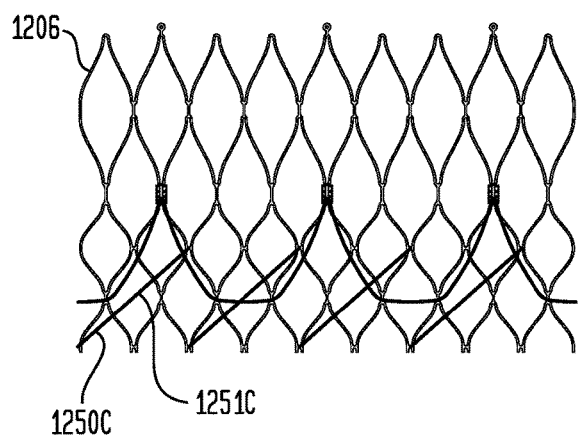
FIGS. 12C-12K are developed views of variations of the stent, sealing ring, and leaflets of FIG. 12A.

FIG. 12C shows a sealing ring 1250C that is the same as the sealing ring 1250 of FIGS. 12A-12B, except that the sealing ring 1250C includes four discontinuous sections 1251C, each such section extending around part of the circumference of the stent 1206. As shown in FIG. 12C, each section 1251C extends around ⅔ of the circumference of the stent 1206, such that the four discontinuous sections together extend around ⅘ of the circumference of the stent, leaving ⅕ of the circumference of the stent without a portion of the sealing ring 1250C. In other embodiments, each of the four sections 1251C may extend around ¼ of the circumference of the stent 1206, so that the four sections together extend around the entire circumference of the stent.

Figure 12D:
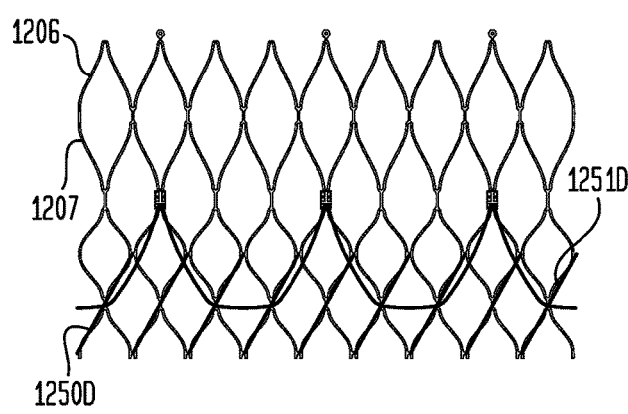

FIG. 12D shows another sealing ring 1250D that is the same as the sealing ring 1250 of FIGS. 12A-12B, except that the sealing ring 1250D includes nine discontinuous sections 1251D. Each section 1251D extends around about ⅑ of the circumference of the stent 1206, so that the nine sections together extend around the entire circumference of the stent 1206. As can be seen in FIG. 12D, each section 1251D of the sealing ring 1250D may be attached to the stent 1206 and the cuff 1212 along the contour of certain struts 1207.

Figure 12E:
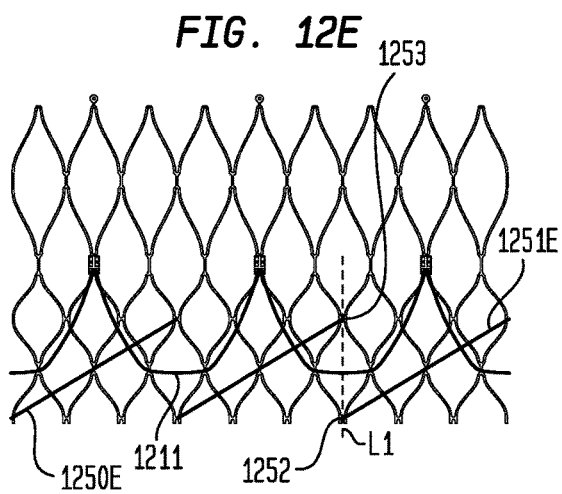

FIG. 12E shows a further sealing ring 1250E that is the same as the sealing ring 1250 of FIGS. 12A-12B, except that the discontinuous sections 1251E are circumferentially offset relative to the locations of the discontinuous sections 1251 of FIGS. 12A-12B. As shown in FIG. 12E, the imaginary vertical line L1 that intersects the high end 1253 of one section 1251E and the low end 1252 of the adjacent discontinuous section may extend through or very close to the lowest attached portion 1211 of a corresponding one of the bellies of the leaflets 1210.

Figure 12F:
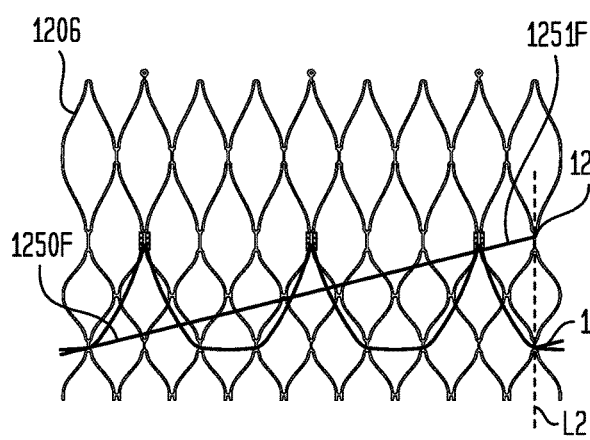

FIG. 12F shows yet another sealing ring 1250F that is the same as the sealing ring 1250 of FIGS. 12A-12B, except that the sealing ring 1250F includes a single discontinuous section 1251F. The single discontinuous section 1251F extends around the entire circumference of the stent 1206. The high end 1253 of the section 1251F is aligned in the flow direction with, but vertically displaced from, the low end 1252 of the section, such that an imaginary line L2 can be drawn in the flow direction that intersects the high end and the low end of the section.

Figure 12G:
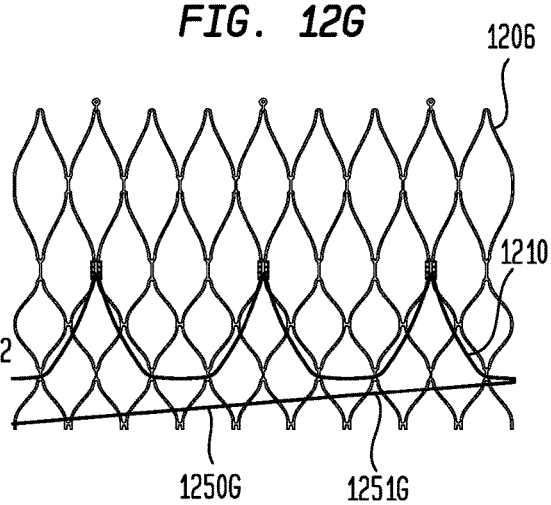

FIG. 12G shows a sealing ring 1250G that is the same as the sealing ring 1250F of FIG. 12F, but positioned lower on the stent 1206. That is, the sealing ring 1250G is attached to the stent 1206 and cuff 1212 so as to lie entirely below the positions at which the bellies of the leaflets 1210 are attached to the stent and cuff.

Figure 12H:
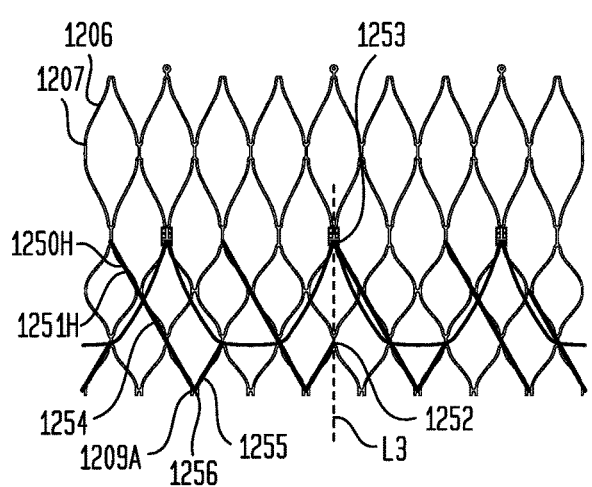

FIG. 12H shows a sealing ring 1250H that is a variant of the sealing ring 1250 of FIGS. 12A-12B. The sealing ring 1250H similar to the sealing ring 1250 of FIGS. 12A-12B, except that the sealing ring 1250H includes five discontinuous sections 1251H that together extend around the entire circumference of the stent 1206. Three of the discontinuous sections 1251H each extend around about ⅖ of the circumference of the stent 1206, and the remaining two discontinuous sections each extend around about ⅙ of the circumference of the stent.

As shown in FIG. 12H, the high end 1253 of each section 1251F is aligned in the flow direction with, but vertically displaced from, the low end 1252 of an adjacent discontinuous section, such that an imaginary line L3 can be drawn in the flow direction that intersects the high end of one section and the low end of an adjacent discontinuous section. The discontinuous sections 1251H together extend around the entire circumference of the stent without any significant overlap in the flow direction. Each section 1251H of the sealing ring 1250H may be attached to the stent 1206 and the cuff 1212 along the contour of certain struts 1207. Some of the sections 1251H have a falling portion 1254 and a rising portion 1255 that meet at a vertex 1256 at the proximalmost junctions 1209A of the stent 1206.

Figure 12I:
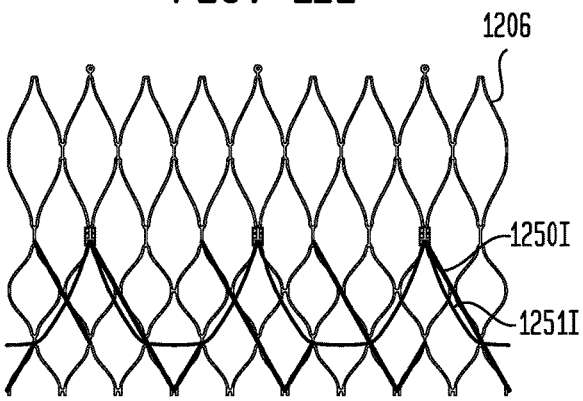

FIG. 12I shows a sealing ring 1250J that is the same as the sealing ring 1250H of FIG. 12H, except that the sealing ring 1250J includes five discontinuous sections, four of which each extend around about ⅖ of the circumference of the stent 1206, and the remaining one of which extends around about ⅙ of the circumference of the stent. Similar to the discontinuous sections 1251H, the sections 1251I together extend around the entire circumference of the stent without any significant overlap in the flow direction.

Figure 12J:
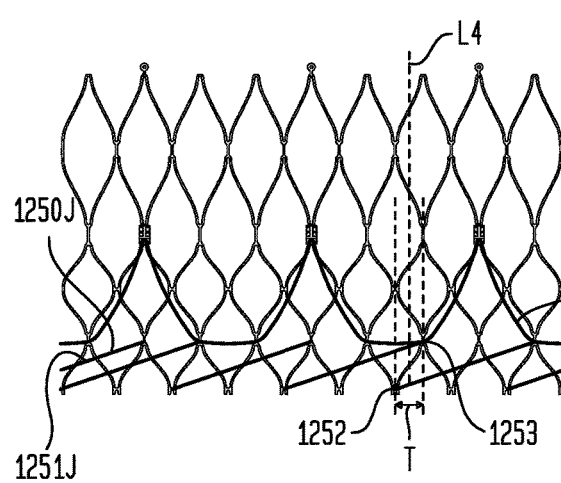

FIG. 12J shows a sealing ring 1250J that is a variant of the sealing ring 1250 of FIGS. 12A-12B. The sealing ring 1250J is similar to the sealing ring 1250 of FIGS. 12A-12B, except that the sealing ring 1250J includes five discontinuous sections 1251J, each section extending around part of the circumference of the stent 1206 and partially overlapping the adjacent section in the circumferential direction.

As shown in FIG. 12J, each discontinuous section 1251J extends around ⁵⁄₁₈ of the circumference of the stent 1206 and overlaps the adjacent discontinuous section by at least ¹⁄₁₈ of the circumference of the stent, such that the five discontinuous sections together extend around the entire circumference of the stent 1206. The high end 1253 of each discontinuous section 1251J overlaps the low end 1252 of an adjacent discontinuous section in the circumferential direction by at least an amount T, such that an imaginary line L4 in the flow direction can be drawn within the circumferentially overlapping area that intersects both discontinuous sections.

In the embodiment of FIG. 12J, the discontinuous sections 1251J of the sealing ring 1250J are attached to the stent 1206 and cuff 1212 so as to lie entirely below the positions at which the bellies of the leaflets 1210 are attached to the stent and cuff. In other embodiments (e.g., FIG. 12K), that need not be the case.

Figure 12K:
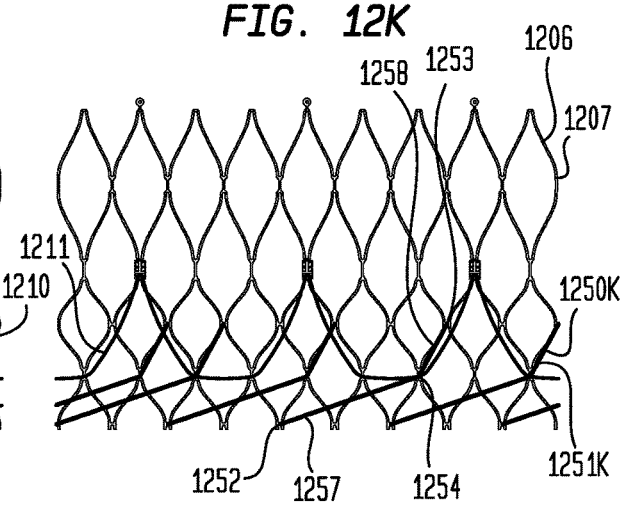

FIG. 12K shows a sealing ring 1250K that is the same as the sealing ring 1250J of FIG. 12J, except that each discontinuous section 1251K has a first portion 1257 that extends from the low end 1252 to a vertex 1254, and a second portion 1258 that extends from the vertex to the high end 1253. The first portion 1257 does not follow the contour of the struts 1207, while the second portion 1258 is attached to the stent 1206 and cuff 1212 along the contour of certain ones of the struts, thereby forming each section 1251K with a dogleg shape. As can be seen in FIG. 12K, each section 1251K may extend from a location below the lowest point at which the bellies of the leaflets 1210 are attached to the stent 1206 and cuff 1212 to a location above that lowest point.

FIGS. 13A-13E illustrate prosthetic heart valve configurations that have embodiments of sealing rings that are variants of the sealing ring 850 shown in FIGS. 8A-8B, in which the sealing ring embodiments have a plurality of separately formed portions that may or may not be discontinuous with one another.

Figure 13A:
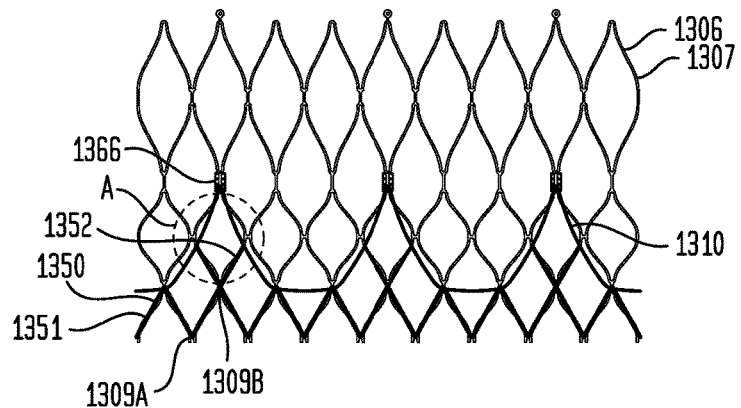
FIG. 13A is a developed view of the stent, sealing ring, and leaflets of another embodiment of a heart valve having a sealing ring intended to fill irregularities between the heart valve and the native valve annulus.

FIG. 13A shows a sealing ring 1350 that is a variant of the sealing ring 850 of FIGS. 8A-8B (and a variant of the sealing ring 550C of FIG. 5C). The sealing ring 1350 is the same as the sealing ring 850 of FIGS. 8A-8B, except that the sealing ring 1350 includes a continuous portion 1351 and three discrete portions 1352 disposed adjacent the continuous portion. The continuous portion 1351 and the discrete portions 1352 may be formed separately and attached to the stent 1306 adjacent one another, or they may be formed together as a single continuous piece of fabric, for example.

As can be seen in FIG. 13A, the continuous portion 1351 has the zigzag shape of the sealing ring 550C shown in FIG. 5C, and extends completely around the circumference of the stent 1306. The continuous portion 1351 is attached to the stent 1306 and the cuff following the zigzag contour of the proximalmost struts 1307 of the stent 1306.

Each of the three discrete portions 1352 of the sealing ring 1350 points down and is aligned below a corresponding commissure feature 1366 in the flow direction. Each portion 1352 may be attached to the stent 1306 and the cuff following the contour of the struts 1307 between the continuous portion 1351 and the locations where the bellies of the leaflets 810 are attached to the stent and cuff. An exemplary portion 1352 is shown in the circle A in FIG. 13A.

As shown in FIG. 13A, the continuous portion 1351 and the discrete portions 1352 may be attached to the stent 1306 and cuff entirely below the locations at which the bellies of the leaflets 1310 are attached to the stent and cuff. In other embodiments, that need not be the case.

Figure 13B:
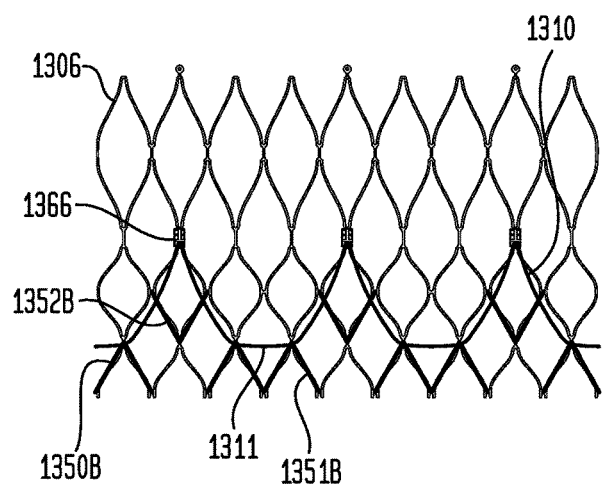
FIGS. 13B-13E are developed views of variations of the stent, sealing ring, and leaflets of FIG. 13A.

FIG. 13B shows a sealing ring 1350B that is the same as the sealing ring 1350 of FIG. 13A, except that, rather than a continuous portion that extends completely around the circumference of the stent 1306, the sealing ring 1350B includes three lower discrete portions 1351B that are spaced from one another in the circumferential direction. The sealing ring 1350B also includes three upper discrete portions 1352B that point down and are disposed longitudinally above the row of discrete portions 1351B, but above the spaces between adjacent ones of the portions 1351B.

The three upper discrete portions 1352B are disposed in the same locations on the stent 1306 as the three discrete portions 1352 shown in FIG. 13A, and are generally aligned in the flow direction below a corresponding commissure feature 1366. The three lower discrete portions 1351B are disposed on portions of the stent 1306 circumferentially offset from the three upper discrete portions, and are generally aligned in the flow direction with the lowest portions 1311 at which the bellies of the leaflets 1310 are attached to the stent 1306 and the cuff. Each of the upper discrete portions 1352B extends around about ⅓ of the circumference of the stent 1306, and each of the lower discrete portions 1351B extend around about ⅔ of the circumference of the stent, such that together, the upper and lower discrete portions extend around the entire circumference of the stent.

Figure 13C:
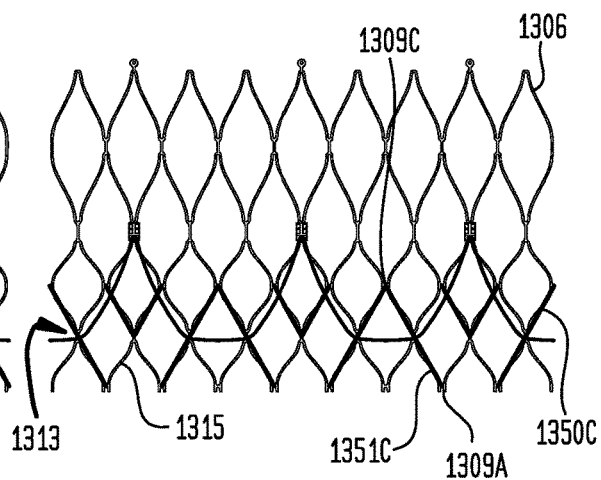

FIG. 13C shows a sealing ring 1350C that is the same as the sealing ring 1350B of FIG. 13B, except that, rather than forming two peaks, the three lower discrete portions 1351C each form a single peak that extends farther from the proximal end of the stent. That is, each lower discrete portion 1351C points up and extends from the proximalmost junctions 1309A of the stent 1306 to the upper junctions 1309C of certain cells in the first full row 1313 of complete cells 1315, such that each lower discrete portion extends both above and below the locations at which the bellies of the leaflets 1310 are attached to the stent 1306 and cuff.

Figure 13D:
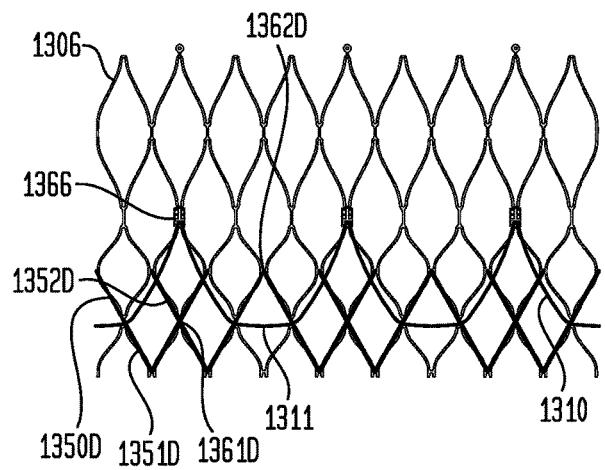

FIG. 13D shows another sealing ring 1350D that is similar to the same as the sealing ring 1350 of FIG. 13A, except that the continuous portion 1351D has the same alternating height zigzag shape as the sealing ring 950 shown in FIG. 9A. The continuous portion 1351D has low peaks 1361D substantially aligned in the flow direction with the commissure features 1366 and with the upper discrete portions 1352D, and high peaks 1362D substantially aligned in the flow direction with the lowest attached portions 1311 of the bellies of the leaflets 1310. Like the sealing ring 950 of FIG. 9A, the continuous portion 1351D extends both above and below the locations at which the bellies of the leaflets 1310 are attached to the stent 1306 and cuff. The three upper discrete portions 1352D of the sealing ring 1350D may be the same as the discrete portions 1352 of FIG. 13A.

Figure 13E:
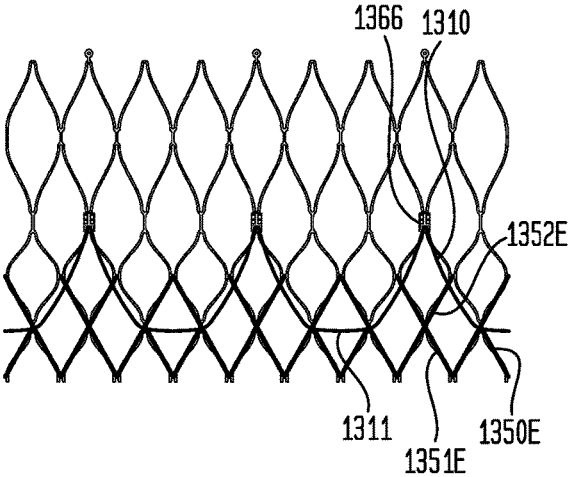

FIG. 13E shows a further sealing ring 1350E that is similar to the sealing ring 1350 of FIG. 13A, except that the sealing ring 1350E includes six discrete portions 1352E disposed above the continuous portion 1351E. Three of the discrete portions 1352E are the same as the discrete portions 1352 of FIG. 13A, which point down and are each substantially aligned in the flow direction with a corresponding commissure feature 1366. The other three discrete portions 1352E point up and are disposed between the discrete portions just described, and are substantially aligned in the flow direction above the lowest attached portions 1311 of the bellies of the leaflets 1310.

Figure 14A:
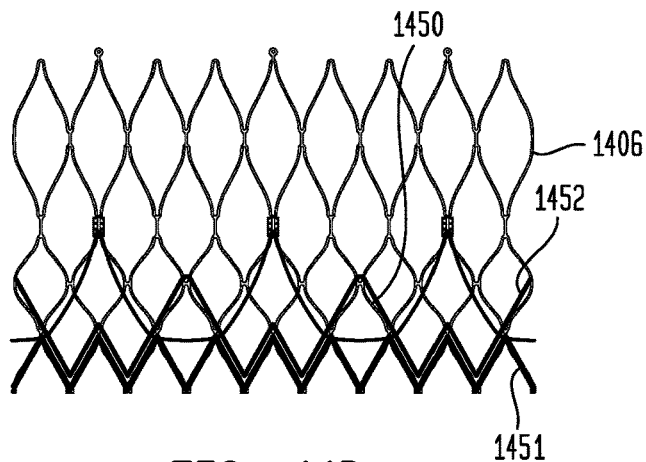
FIG. 14A is a developed view of the stent, sealing ring, and leaflets of another embodiment of a heart valve having a sealing ring intended to fill irregularities between the heart valve and the native valve annulus.
Figure 14B:
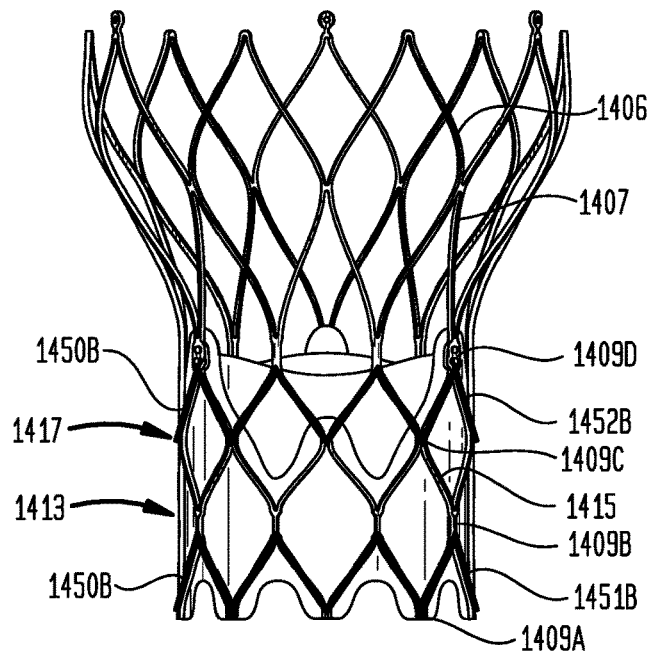
FIG. 14B is a side view of a variation of the stent, sealing ring, and leaflets of FIG. 14A.
Figure 14C:
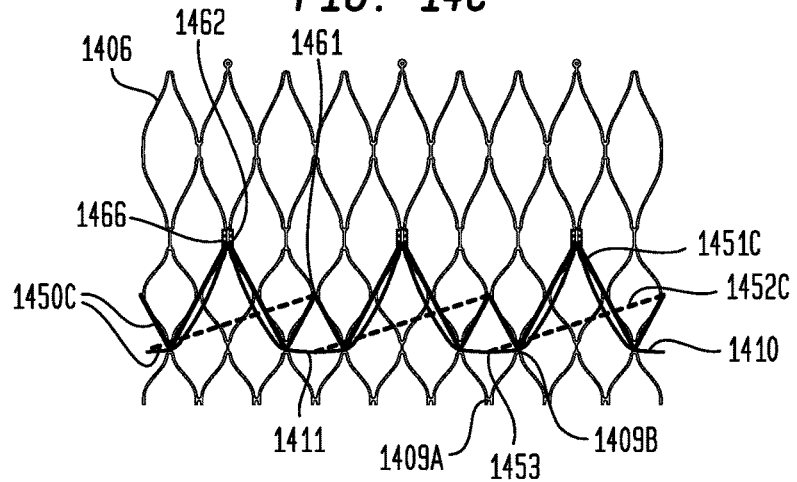
FIG. 14C is a developed view of another variation of the stent, sealing ring, and leaflets of FIG. 14A.

FIGS. 14A-14C illustrate prosthetic heart valve configurations that have embodiments of sealing rings that are variants of the sealing rings shown and described above, in which the sealing ring embodiments include two sealing ring members each extending around the circumference of the stent.

FIG. 14A shows a sealing ring 1450 that is a variant of the sealing ring 950 of FIGS. 9A-9B. The sealing ring 1450 has a lower continuous member 1451 and an upper continuous member 1452 adjacent thereto. The upper continuous member 1452 has the same alternating height zigzag shape as the sealing ring 950 shown in FIG. 9A, while the lower continuous member 1451 has the same zigzag shape as the sealing ring 550C shown in FIG. 5C. The lower member 1451 and the upper member 1452 may be formed separately and attached to the stent 1406 adjacent one another, or they may be formed together as a single continuous piece of fabric, for example.

FIG. 14B shows a sealing ring 1450B that is a variant of the sealing ring 450C of FIG. 4C. The sealing ring 1450B has a lower continuous member 1451B and an upper continuous member 1452B adjacent thereto. The upper member 1451B and the lower member 1452B have the same zigzag shape as the sealing ring 550C shown in FIG. 5C and are spaced apart from one another in the flow direction of the stent 1406. It is preferred that the lower member 1451B and the upper member 1452B of the sealing ring 1450B be attached to a cuff having a higher cuff height in the flow direction of the stent 1406, such as the cuff 712 of FIG. 7.

The lower member 1451B is attached to the stent 1406 and the cuff following the zigzag contour of certain struts 1407 between the proximalmost junctions 1409A of the stent, and the upper junctions 1409B of the proximalmost struts of the stent. The upper member 1452B may be attached to the stent 1406 and the cuff following the zigzag contour of certain struts 1407 between the upper junctions 1409C of the first full row 913 of complete cells 915 and the upper junctions 1409D of the second full row 1417 of complete cells 1415 above the first full row.

FIG. 14C shows a sealing ring 1450 that is a variant of the sealing ring 950 of FIGS. 9A-9B. The sealing ring 1450C has a continuous member 1451C and discontinuous sections 1452C that partially overlap one another.

The continuous member 1451C has the same alternating height zigzag shape as the sealing ring 950 shown in FIG. 9A, but is shifted longitudinally and circumferentially on the stent 1406 so that the high peaks intersect with the commissure features 1466. That is, the low peaks 1461 are substantially aligned in the flow direction with the lowest attached portions 1411 of the bellies of the leaflets 1410, while the high peaks 1462 are substantially aligned in the flow direction with the commissure features 1466. The low peaks 1461 are disposed at the upper junctions 1409C of the first full row 1413 of complete cells 1415, and the high peaks 1462 are disposed at the commissure features 1466 which are at the upper junctions 1409D of the second full row 1417 of complete cells 1415 above the first full row.

The discontinuous sections 1452C are the same as the discontinuous sections 1251E of FIG. 12E, but the low end 1453 of each discontinuous section may be attached approximately at the height of the upper junctions 1409B of the proximalmost struts 1407 of the stent 1406, rather than being attached at the proximalmost junctions 1409A of the stent.

Although the various sealing structures have been described herein as "sealing rings," it is to be understood that the term "sealing ring" as used herein may describe one or more discontinuous sealing structures that do not completely extend around the circumference of the stent of a prosthetic heart valve.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A prosthetic heart valve configured to be expanded in a native aortic annulus of a patient, the prosthetic heart valve comprising:
   a collapsible and expandable stent extending between a proximal end and a distal end, the stent including an annulus section adjacent the proximal end and a plurality of struts shaped to form a plurality of cells connected to one another in a plurality of annular rows around the stent, the stent having a longitudinal axis and a flow direction from the proximal end toward the distal end;
   a cuff attached to the annulus section of the stent;
   a plurality of prosthetic valve leaflets each having a belly attached to the cuff between a first location and a second location downstream from the first location in the flow direction, the belly of each leaflet including a lowest attached portion that is closest to the proximal end of the stent;
   a quantity of commissure features on the stent, each of the commissure features being located at a junction of two adjacent leaflets; and
   a sealing ring attached around an exterior surface of the annulus section of the stent, the sealing ring having a diameter greater than a diameter of the proximal end of the stent when the stent is in an expanded condition, the sealing ring having an undulating configuration with a number of sealing ring peaks and a number of sealing ring valleys, the sealing ring valleys extending linearly in a direction substantially orthogonal to the longitudinal axis of the stent when the stent is in the expanded condition, the sealing ring valleys being closer to the proximal end of the stent than the sealing ring peaks, each of the sealing ring valleys being disposed between the lowest attached portions of two adjacent leaflets as one proceeds in a circumferential direction around the stent.

2. The prosthetic heart valve as claimed in claim 1, wherein the sealing ring valleys are attached to the cuff.

3. The prosthetic heart valve as claimed in claim 1, wherein the sealing ring valleys are not attached to the cuff or the stent.

4. The prosthetic heart valve as claimed in claim 3, wherein tension in the sealing ring valleys when the stent is in the expanded condition support the sealing ring valleys so that the sealing ring valleys extend linearly in the direction substantially orthogonal to the longitudinal axis of the stent.

5. The prosthetic heart valve as claimed in claim 1, wherein the sealing ring peaks are substantially aligned in the flow direction with the lowest attached portions of the leaflets.

6. The prosthetic heart valve as claimed in claim 5, wherein each of the sealing ring valleys is substantially aligned in the flow direction with a respective one of the commissure features.

7. The prosthetic heart valve as claimed in claim 1, wherein each of the sealing ring valleys is substantially aligned with the lowest attached portions of the leaflets at a predetermined distance from the proximal end of the stent as one proceeds in the circumferential direction of the stent when the stent is in the expanded condition.

8. The prosthetic heart valve as claimed in claim 1, wherein each of the sealing ring valleys is positioned between the first location and the proximal end of the stent.

9. The prosthetic heart valve as claimed in claim 1, wherein the sealing ring is positioned entirely between the commissure features and the proximal end of the stent.

10. The prosthetic heart valve as claimed in claim 1, wherein each of the sealing ring peaks is V-shaped.

* * * * *